United States Patent
Sanada et al.

[11] Patent Number: 6,084,716
[45] Date of Patent: Jul. 4, 2000

[54] OPTICAL SUBSTRATE INSPECTION APPARATUS

[75] Inventors: Yasushi Sanada, Yokohama; Toru Tojo, Kanagawa-ken; Mitsuo Tabata; Kyoji Yamashita, both of Yokohama; Hideo Nagai, Nagareyama; Noboru Kobayashi, Yokohama; Hisakazu Yoshino, Tochigi-ken; Makoto Taya, Tokyo; Akemi Miwa, Kawaguchi, all of Japan

[73] Assignees: Kabushiki Kaisha Toshiba, Kawasaki; Topcon Corporation, Tokyo, both of Japan

[21] Appl. No.: 09/112,641

[22] Filed: Jul. 9, 1998

[30] Foreign Application Priority Data

| Jul. 9, 1997 | [JP] | Japan | 9-183796 |
| Mar. 23, 1998 | [JP] | Japan | 10-074575 |

[51] Int. Cl.[7] .......................... G02B 27/10; G02B 27/14; G01N 21/88
[52] U.S. Cl. ..................... 359/629; 359/618; 356/237.5
[58] Field of Search ................... 359/618, 629; 356/237.2, 237.5

[56] References Cited

U.S. PATENT DOCUMENTS

| 3,851,951 | 12/1974 | Eveleth | 359/286 |
| 4,849,645 | 7/1989 | Mendenko et al. | 250/563 |
| 5,309,108 | 5/1994 | Maeda et al. | 324/501 |
| 5,528,360 | 6/1996 | Kohno | 356/237 |
| 5,572,598 | 11/1996 | Wihl et al. | 382/144 |
| 5,694,214 | 12/1997 | Watanabe et al. | 356/237 |
| 5,995,219 | 11/1999 | Tabata | 356/237.5 |

FOREIGN PATENT DOCUMENTS

| 6-58873 | 8/1994 | Japan . |
| 6-294750 | 10/1994 | Japan . |
| 6-347416 | 12/1994 | Japan . |

*Primary Examiner*—Georgia Epps
*Assistant Examiner*—Saeed Seyrafi
*Attorney, Agent, or Firm*—Oblon, Spivak, McClelland, Maier & Neustadt, P.C.

[57] ABSTRACT

A single light emitted from a laser source is split into multiple beams. The multiple beams are illuminated by a multi-beam scanner to scan a substrate of interest. An optical system is provided for focusing the multiple beams independently on the substrate and directing a reflected light or a transmitted light of the multiple beams on the substrate. Aperture regulating members are disposed at equal intervals corresponding to the interval between the multiple beams for controlling the multiple beams directed from the substrate by the optical system. The multiple beams passed through their respective aperture regulating members are received by an optical detector assembly which detect a change in the amount of the multiple beams. The substrate is continuously moved by a movable table on a plane substantially vertical to the multiple beams and in a direction arranged at substantially a right angle to the scanning direction of the multiple beams. Then, a scanned image is produced by an image processor from a signal output of the detector assembly and data of the coordinate location of the movable table and compared by a comparator with a corresponding reference image.

21 Claims, 14 Drawing Sheets

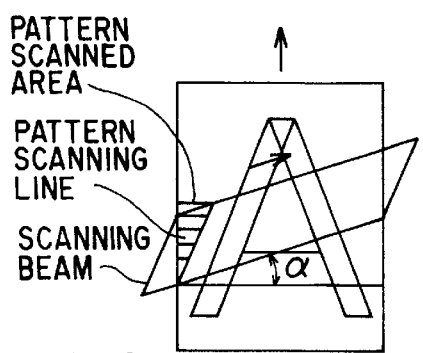
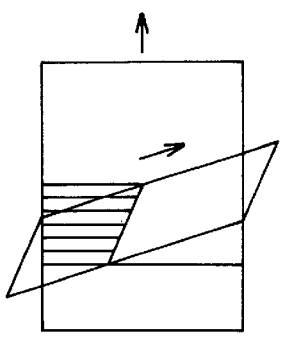
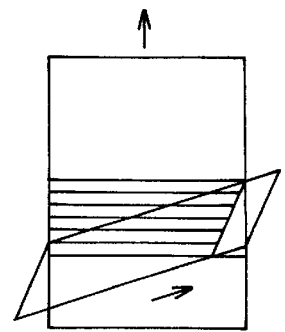
FIG. 6A  FIG. 6B  FIG. 6C
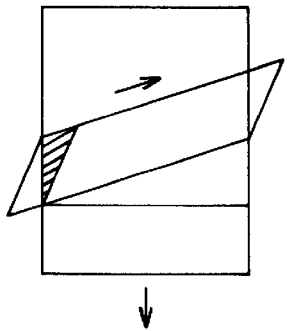
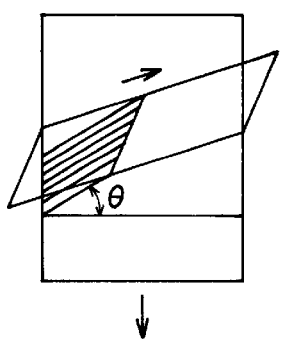
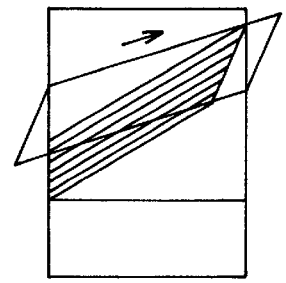
FIG. 6D  FIG. 6E  FIG. 6F
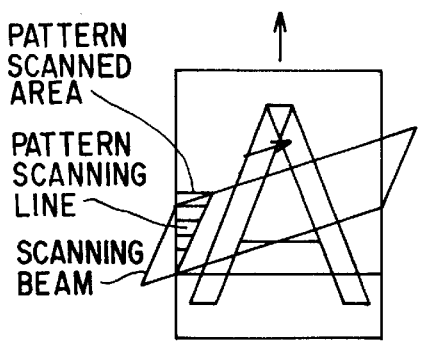
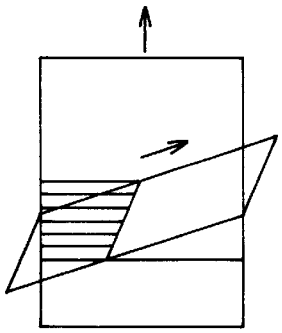
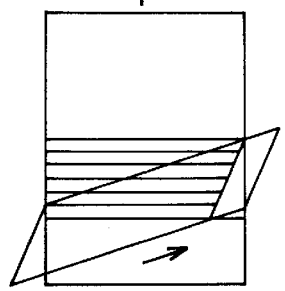
FIG. 7A  FIG. 7B  FIG. 7C
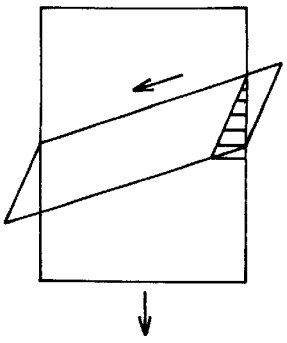
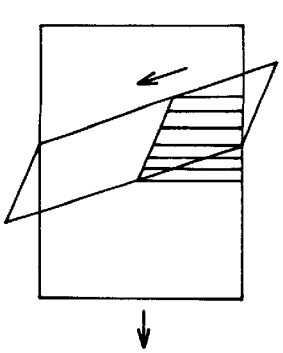
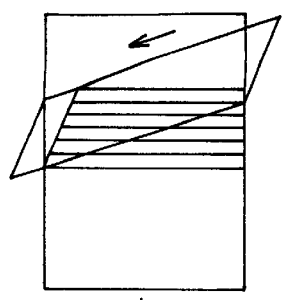
FIG. 7D  FIG. 7E  FIG. 7F

OPTICAL SUBSTRATE INSPECTION APPARATUS

BACKGROUND OF THE INVENTION

The present invention relates to an optical substrate inspection apparatus for inspecting masks (reticules) or wafers having patterns requisite for fabricating semiconductor devices and particularly, to an optical substrate inspection apparatus using multi-beam laser light.

As LSI chips have been increased in the level of integration and the size of capacity, the width of each circuitry line for semiconductor devices is significantly reduced. In the production of such semiconductor devices, a pattern original (mask, reticule) which carries a pattern of circuitry lines is commonly used in a reduced image exposure system, known as a stepper, for printing the pattern on a wafer.

It is however true that the pattern on a mask or a wafer often includes various defects occurring during the fabrication. Those defects may result in malfunction of semiconductor devices and also may decline the productivity. It is essential in the production of semiconductor devices to conduct a step for eliminating such defects or an inspection step for detecting the presence of defects before subjecting to a repair or amendment step.

For the purpose of detecting defects on the pattern, optical substrate inspection apparatuses are widely employed. For example, one of them is disclosed as theutomated photomask inspection apparatus in European Patent Application 0532927A2. Another is depicted in "Mask defect inspection method by data base comparison with 0.25–0.35 µm sensitivity", Jpn. J. Appl. Phys., Vol.33 (1994).

Such a conventional apparatus is however unfavorable because its optical resolution is not of a desirable level and the sensitivity for detection of defects is too low to be accepted. More specifically, any conventional optical substrate inspection apparatus includes an optical system of not a super-resolution type but a common integral-illumination type where the resolution is expressed by $\lambda/NA$ as proportional to the wavelength $\lambda$ and inverse proportional to the numerical aperture NA used for the inspection (with a field of view being illuminated in its entirety).

In that system, the wavelength to be used for the inspection has to be set to a minimum for having an optimum resolution. When the wavelength is minimized to e.g. 250 nm which entails low responsibility of a detector, the integral illumination may be used with a less intensity of illumination and the time for the detection will thus be increased.

Another technique for detecting the defects on the pattern is a laser scanning which can provide a proper amount of laser beam. However, the technique uses a single beam of laser light for scanning over a target area. For providing an acceptable rate of the detection, the scanning with the laser beam has to be carried out at a higher speed. Accordingly, the amount of light fallen on a detector will be lowered and the time for the detection will hardly be decreased.

In the conventional optical substrate inspection apparatuses, the optical resolution gained is rarely as high as desired and the sensitivity for detecting the defects will unfavorably be low. In case that a pattern for an advanced semiconductor device such as a one gigabit DRAM, is developed in the near future, it will hardly be inspected precisely by the conventional apparatus. In the technique of the conventional apparatuses, a shorter wavelength optical system may be exploited for improving the sensitivity for detecting the defects. The fact that the time for the detection is still long cannot be overcome.

It is an object of the present invention to provide an optical substrate inspection apparatus capable of inspecting any defect on a pattern for an advanced semiconductor device (such as a one gigabit DRAM) with a higher level of the optical resolution but not increasing the time for inspection.

BRIEF SUMMARY OF THE INVENTION

The principle of the present invention resides in having a super resolution optical system based on a cofocal optical system assigned as the inspection optical system and allowing multiple beams of light to illuminate and scan a substrate at a high speed for detection of defects of a pattern on the substrate with maintaining the super resolution optical system while the scanned multiple beams received by a detector remaining stationary during the scanning.

According to a first aspect of the present invention, an optical substrate inspection apparatus for illuminating a substrate to be inspected with light and inspecting impurity and defect of a pattern formed on the substrate and/or foreign material adhering on the substrate, comprises:

a laser source for generating a laser light to illuminate the substrate;

a beam splitter for splitting the laser light of the laser source into a plurality of beams;

a multi-beam scanner for scanning the substrate with the multiple beams;

an optical section for focusing the multiple beams independently on the substrate and directing at least one of reflected light and transmitted light of the multiple beams reflected on and transmitted; and an optical detector for detecting a change in the amount of each beam directed by the optical section.

According to a second aspect of the present invention, an optical substrate inspection apparatus for illuminating a substrate to be inspected with light and inspecting impurity and defect of a pattern formed on the substrate and/or foreign material adhering on the substrate comprises:

a laser source for generating a laser light to illuminate the substrate;

a beam splitter for splitting the laser light of the laser source into a plurality of beams aligned at substantially equal intervals;

a multi-beam scanner for scanning the substrate with the multiple beams;

an optical section for focusing the multiple beams independently on the substrate and directing at least one of reflected light and transmitted light of the multiple beams reflected by and transmitted through the substrate;

groups of aperture regulating members disposed between the optical section and the optical detector at equal intervals corresponding to the intervals of the multiple beams directed from the substrate by the optical section for controlling the multiple beams; an optical detector for detecting a change in the amount of each of the multiple beams passed through the aperture regulating members;

a movable table for continuously moving on a plane substantially vertical to the multiple beams and in a direction substantially perpendicular to the scanning direction of the multiple beams;

an image generator for generating a two-dimensional scanned image in accordance with a detection signal from the optical detector and a coordinate location of the movable table; and a comparator for effecting a comparison between the two-dimensional scanned image from the image generator and a two-dimensional reference image.

According to a third aspect of the present invention, an optical substrate inspection apparatus for illuminating a substrate to be inspected with light and inspecting impurity and defect of a pattern formed on the substrate and/or foreign material adhering on the substrate comprises:

a laser source for generating a laser light to illuminate the substrate; a beam splitter for splitting the laser light of the laser source into a plurality of beams aligned at substantially equal intervals; first a multi-beam scanner for scanning the substrate with the multiple beams splitted in first scanning direction;

an image rotator for changing the angle between the first scanning direction determined by the first a multi-beam scanner and the direction of alignment of the multiple beams;

first optical section for focusing the multiple beams independently on the substrate;

second optical section for directing one of reflected light and transmitted light of the multiple beams reflected by and transmitted through the substrate;

groups of aperture regulating members disposed at equal intervals corresponding to the intervals of the multiple beams directed from the substrate by the second optical section for controlling the multiple beams;

an optical detector for detecting a change in the amount of each of the multiple beams passed through the groups of aperture regulating members;

a movable table for continuously moving on a plane substantially vertical to the multiple beams and in a direction substantially perpendicular to the scanning direction of the multiple beams;

an image generator for generating a two-dimensional scanned image in accordance with a detection signal from the optical detector and a coordinate location of the movable table; and a comparator for effecting a comparison between the two-dimensional scanned image from the image generator and a two-dimensional reference image.

The foregoing aspects of the present invention are further featured by the following requirements.

The apparatuses according to the aspects comprises a control circuit for controlling the first a multi-beam scanner or a detector section for measuring a portion of the amount of the multiple beams scanned with the control circuit. The apparatuses designate a portion of signals from electronic section of the control circuit or detection section as the reference signal for use with data signals produced by the scanning with the multiple beams.

Also, the apparatuses according to the aspects comprises a first control circuit for controlling the first a multi-beam scanner or a detector section for measuring a portion of the amount of the multiple beams scanned with the first control circuit. The apparatuses designates a portion of signals from electronic section of the control circuit or detection section as the reference signal for determining the location of the movable table.

Further, the apparatuses according to the aspects is provided an image, as a two-dimensional reference image, produced from design data of the pattern or a preceding scanned image is utilized for the inspection.

Moreover, the apparatuses according to thespects is provided that the angle between the first scanning direction and the direction of alignment of the multiple beams is substantially 5° or less.

According to a fourth aspect of the present invention, an optical substrate inspection apparatus for illuminating a substrate to be inspected with light and inspecting impurity and defect of a pattern formed on the substrate and/or foreign material adhering on the substrate comprises: a laser source for generating a laser light to illuminate the substrate; a beam splitter for splitting the laser light of the laser source into a plurality of beams aligned at substantially equal intervals; a multi-beam scanner for scanning the substrate with the multiple beams; an optical section for focusing the multiple beams independently on the substrate and directing at least one of reflected light and transmitted light of the multiple beams reflected on and transmitted through the substrate; and an optical detector for detecting a change in the amount of the transmitted light and the reflected light separately directed by the optical section.

The apparatus according to fourth aspect of the present invention is provided that the optical detector comprises a first optical detector for detecting a change in the amount of the multiple beams from the reflected light and a second optical detector for detecting a change in the amount of the multiple beams from the transmitted light. In particular, the first optical detector is arranged to detect a change in the amount of the multiple beams passed through the aperture regulating members which are located at intervals corresponding to the intervals of the multiple beams from the substrate.

The apparatus may also be modified for selectively detecting the reflected light and the transmitted light separately or simultaneously.

The apparatus may be modified further comprising either a section for directing at least portions of the reflected light and the transmitted light in a combination to any of the first and second optical detectors or a third optical detector for detecting at least portions of the reflected light and the transmitted light in a combination.

The apparatus may be modified further comprising mirror section provided across the optical path in the rear of the substrate for reflecting only the transmitted light which is then passed again through the substrate, reflected by the mirror section, and received by the second an optical detector.

The apparatus may be modified further comprising a substrate thickness compensating mechanism for geometrically compensating an aberration change in the optical section derived from the thickness of the substrate and a substrate thickness measuring section for at least anticipating the thickness of the substrate, wherein the amount of the transmitted light of the multiple beams is detected by the optical detector.

According to fifth aspect of the present invention, an optical substrate inspection apparatus for illuminating a substrate to be inspected with light and inspecting impurity and defect of a pattern formed on the substrate and/or foreign material adhering or the substrate comprises:

a laser source for generating a laser light to illuminate the substrate;

a beam splitter for splitting the laser light of the laser source into a plurality of beams aligned at substantially equal intervals;

first a multi-beam scanner for scanning the substrate with the multiple beams;

a first an optical section for focusing the multiple beams independently on the substrate and directing a reflected light of the multiple beams reflected by the substrate;

a first an optical detector for detecting a change in the amount of the multiple beams directed by the first an optical section;

second a multi-beam scanner arranged operable substantially in synchronism with the first a multi-beam scanner for scanning the transmitted light from the substrate; second an optical section for directing the transmitted light of the multiple beams transmitted through the substrate; and second detecting section for detecting a change in the amount of the multiple beams directed separately by the second a multi-beam scanner and the second an optical section.

The second a multi-beam scanner may preferably be actuated at substantially the same cycle as of the first a multi-beam scanner and in phase with or an integer multiple of 180° out of phase from the first a multi-beam scanner. Also, the first and second a multi-beam scanner may be resonance type scanners; at least one of the scanners having a temperature changing section which controls the temperature for matching the natural frequency of the first a multi-beam scanner with that of the second a multi-beam scanner.

According to a sixth aspect of the present invention, an optical substrate inspection apparatus for illuminating a substrate to be inspected with light and inspecting defect of a pattern formed on the substrate and/or foreign material adhering on the substrate comprises:

a laser source for generating a laser light to illuminate the substrate;

a multi-beam scanner for scanning the substrate with the laser light emitted from the laser source;

an optical section for focusing the laser light on the substrate and directing either of reflected light and transmitted light of the laser light reflected by and transmitted through the substrate; and an optical detector for detecting a change in the amount of the laser light directed by the optical section. In particular, the optical detector includes a plurality of photosensitive elements. In response to the location of scanning of the laser light on the substrate, one of the photosensitive elements or one of signal outputs of the photosensitive elements can be selected and utilized.

According to a seventh aspect of the invention, an optical substrate inspection apparatus for illuminating a substrate to be inspected with light and inspecting defect of a pattern formed on the substrate and/or foreign material adhering on the substrate comprises: a laser source for generating a laser light to illuminate the substrate; a beam splitter for splitting the laser light of the laser source into a plurality of beams; a multi-beam scanner for scanning the substrate with the multiple beams; an optical section for focusing the multiple beams independently on the substrate and directing either of reflected light and transmitted light of the multiple beams reflected on and transmitted through the substrate; and an optical detector for detecting a change in the amount of the multiple beams directed by the optical section. In particular, the optical detector comprises a plurality of photosensitive elements. In response to the location of scanning of the multiple beams on the substrate, one of the photosensitive elements or one of signal outputs of the photosensitive elements can be selected and utilized.

It is preferable that any of the optical systems is arranged so that the size of the photosensitive element is in cofocal relationship with the diameter of a beam spot projected on the substrate.

According to first to fourth aspects of the present invention, the super resolution optical system improves the resolution of a scanned image produced from observation of the pattern and offers a higher level of the amount of a detection signal indicative of a minimal defect than that of the conventional optical systems. Also, the scanning is shifted from a single beam mode to a multi-beam mode with integral illumination while the super resolution optical system is maintained for detection of the signals. This will eliminate decreasing of the amount of light on the detectors and a difficulty in the high-speed response action, thus preventing the decrease of the inspection speed. It is expected that the inspection with the use of a shorter wavelength of light is required by a variety of industries. The optical system in the inspection apparatus of the present invention is favorably applicable to such requirements.

According to the present invention, the traveling movement of the table is optimized and most of its operating time will be shared with effective time steps of the inspection. The defect inspection apparatus of the present invention will thus be increased in the operating speed while minimizing the downtime caused by the table traveling. Also, the S/N ratio of a signal output of the detector is enhanced hence reducing the defect reading of a noise as a defect or the generation of so called a quasi error. This permits the inspection apparatus to enjoy a higher operational reliability in the inspection process.

According to the present invention, the length of the optical path in the system can be changed depending on variations of the thickness of the substrate to be inspected attributed to the type, the allowance, and the flatness. The multi-beam scanning substrate inspection apparatus is thus implemented using a transmission type cofocal optical system.

According to the present invention, the detection of a reflected light and a transmitted light is carried out independently or simultaneously in the multi-beam scanning optical system. More specifically, the cofocal optical system in the apparatus contributes to the increase of the sensitivity for detection of the reflected light so that defect and dust on the pattern of the substrate which are commonly detected by the transmission type optical system in the prior art can be detected by the action of the reflection type optical system-double check is enabled. Also, as the detection of defect and dust is optically conducted through the transmitted and reflected lights, a more number of detection signals are produced and used for comparison than that produced from either the transmitted light or the reflected light. The signals can thus be examined in three dimensions as compared with two dimensions of the conventional apparatus, hence facilitating the judgment whether a defect or a dust is detected and if the dust, which type of the dust is present.

The apparatus permits the detection of the transmitted light to be performed with the cofocal optical system, thus having a higher level of the sensitivity for detection than the conventional apparatus. In addition, the reflected light and the transmitted light are detected simultaneously, hence reducing the inspection time to theoretically ½. This contributes to the increase of the throughput of the apparatus as a production machine and the decrease of the production cost of the same.

According to a fifth aspect of the present invention, the cofocal optical system is used in an ideal mode for detection of the transmitted light. For implementing an ideal mode of the cofocal optical system in the defect inspection apparatus regardless of the use of reflected light and/or transmitted light, the multiple beams scanned over the substrate at a high speed in the main scanning direction are received in their stationary state by their respective detectors. More particularly, the multiple beams are passed through tiny pinholes or flux regulators before received by the detectors in the cofocal optical system. It is essential in the scanning optical system of the inspection apparatus of the present invention that the multiple beams emitted in a stationary condition from a light source are scanned over the substrate and then received by the detectors in the initial condition.

For the purpose, the reflected light reflected by the substrate is shifted back to the stationary condition by the action of an optical path disposed from the light source to the substrate before received by the detectors. The light emitted from the light source is in the stationary condition and polarized by the optical scanning section such as a polygon mirror, a galvanomirror, or an acousto-optic device. The polarized light released from the optical scanning section is reflected by the substrate and passed again through the scanning section where its polarized condition is canceled.

However, the transmitted light is hardly treated by the same manner as of the reflected light. In general, the transmitted light passed through the substrate is directed to the optical scanning section via an extra relay optical system bypassing the substrate. This surely increases the overall arrangement of the optical system as compared with the reflection type optical system. Assuming that the substrate is gradually increased in the size in the future, the bypass of the optical system has to be enlarged proportionally. The enlargement of the optical system may entail a bulky structure of the inspection apparatus as well as the increase of optical load. In addition, the ambient conditions (temperature, moisture, and cleanness) of the inspection apparatus will also be affected thus requiring, for example, the use of a thermal chamber of a considerable size. Also, the space for installation of the inspection apparatus will be increased hence declining the space saving.

Since the relay optical system is needed, the number of optical components including lenses and mirrors is increased and thus, the cost as well as the loss of the light intensity will be soared. The loss of the light intensity may be compensated by the use of a higher power laser. Of course, the increase of energy consumption and laser price will follow. Those disadvantages are critical to not only the performance of the inspection apparatus but also its production cost. While considering that the production cost of the conventional apparatus is high, the defect inspection apparatus of the present invention is intended as a production machine for increasing the performance and decreasing the production cost simultaneously.

The substrate inspection apparatus according to the present invention employs the above described optical system in which an ideal mode of the transmission type cofocal optical system is provided for improving the performance of inspection, minimizing the overall dimensions, and reducing the production cost.

According to sixth and seventh aspects of the present invention, an ideal mode of the cofocal optical system is realized. It is common for implementing the defect inspection apparatus with an ideal mode of the cofocal optical system regardless of the use of transmitted light and/or reflected light that the multiple beams scanned at a high speed in the main scanning direction and the subscanning direction have to be shifted back to their stationary condition after the substrate. For the purpose, tiny pinholes or flux regulators are used in the cofocal optical system of the inspection apparatus. More specifically, it is essential that the multiple beams emitted from a light source are used for scanning over the substrate and then shifted back to a stationary condition before directed to their respective detectors in the scanning optical system of the inspection apparatus.

The reflected light reflected by the substrate can be received in the stationary condition by the detectors after passed through the optical scanning section two times in its forward and backward directions in an optical path extending from the light source to the substrate. The light emitted from the light source is in the stationary condition and polarized by the optical scanning section such as a polygon mirror, a galvanomirror, or an acousto-optic device. The polarized light released from the optical scanning section is reflected by the substrate and passed again through the scanning section where its polarized condition is canceled.

However, the number of optical components through which the light is passed from the light source to the detector is substantially doubled as compared with an apparent number. The amount of the light is declined every time when it passes through an optical device and the actual loss will be greater than apparent loss. For the detector receiving a proper amount of the light, the power of the light source has to be increased. This thus results in increase of the size of the light source and the enlargement of the light source may entail a bulky structure of the optical system or the inspection apparatus. Accordingly, the price of the apparatus will be soared and the efficiency of space utilization at a factory will be declined hence increasing the production cost. As the output of the light source is increased, its higher energy concentration runs through optical components near the light source. As the result, damage to the optical components and thus the substrate to be inspected may be inevitable.

The detection of the transmitted light similar to the reflected light has some drawbacks. For example, the optical system allowing the transmitted light passed through the substrate to be bypassed the substrate before directed back to the optical scanning section is bulky in the arrangement and may be greater than that the reflection type optical system. The number of optical components through which the light is passed is higher in the transmission type optical system than in the reflection type optical system. The physical space requirement is also increased by the structure of the bypass. The overall size of the transmission type optical system will hence be greater than that of the reflected type. Assuming that the substrate and the bypass structure are gradually increased in the size in the future, the overall dimensions of the inspection apparatus will significantly be increased.

The increase of the size of the optical system may be offset by adding the second scanning section designed for canceling the polarization of the light before directing the light to the detector to the common scanning section which shifts the polarization of the light in scanning on the substrate. But, oscillation factor will increase. Such oscillation is substantially critical to the optical system for elaborate inspection. Particularly, the cofocal optical system having a higher level of the sensitivity for detection may seriously be declined in the performance by the effect of oscillation.

As described, the cofocal optical system for optical scanning has been regarded unfavorable for use in the inspection apparatus because of its bulky structure and possibility for creating oscillation, in spite of its higher performance.

The present invention provides the best use of the cofocal optical system for realizing an ideal mode of the transmission type cofocal optical system to increase the performance of inspection, minimizing the overall dimensions, and reducing the production cost of the inspection apparatus.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 6A to 6F are diagrams showing steps of beam scanning on a substrate with a scanner of which scanning direction is limited to one direction;

FIGS. 7A to 7F are diagrams showing steps of beam scanning over the substrate according to the embodiment;

DETAILED DESCRIPTION OF THE INVENTION

Embodiments of the present invention will be described in more detail referring to theccompanying drawings.

An optical substrate inspection apparatus according to the present invention is provided of a novel cofocal multi-beam type in which a plurality of light beams are focused on a substrate and scanned over a pattern in one direction or the main scanning direction at a high speed while a table is traveled in a sub-scanning direction arranged at a right angle to the main scanning direction.

(First Embodiment)

The description starts with explaining a laser cofocal optical system employed for improving the resolution characteristic as a feature of the present apparatus and a multi-beam scanning optical system employed for minimizing the time for inspection.

Figure 1:
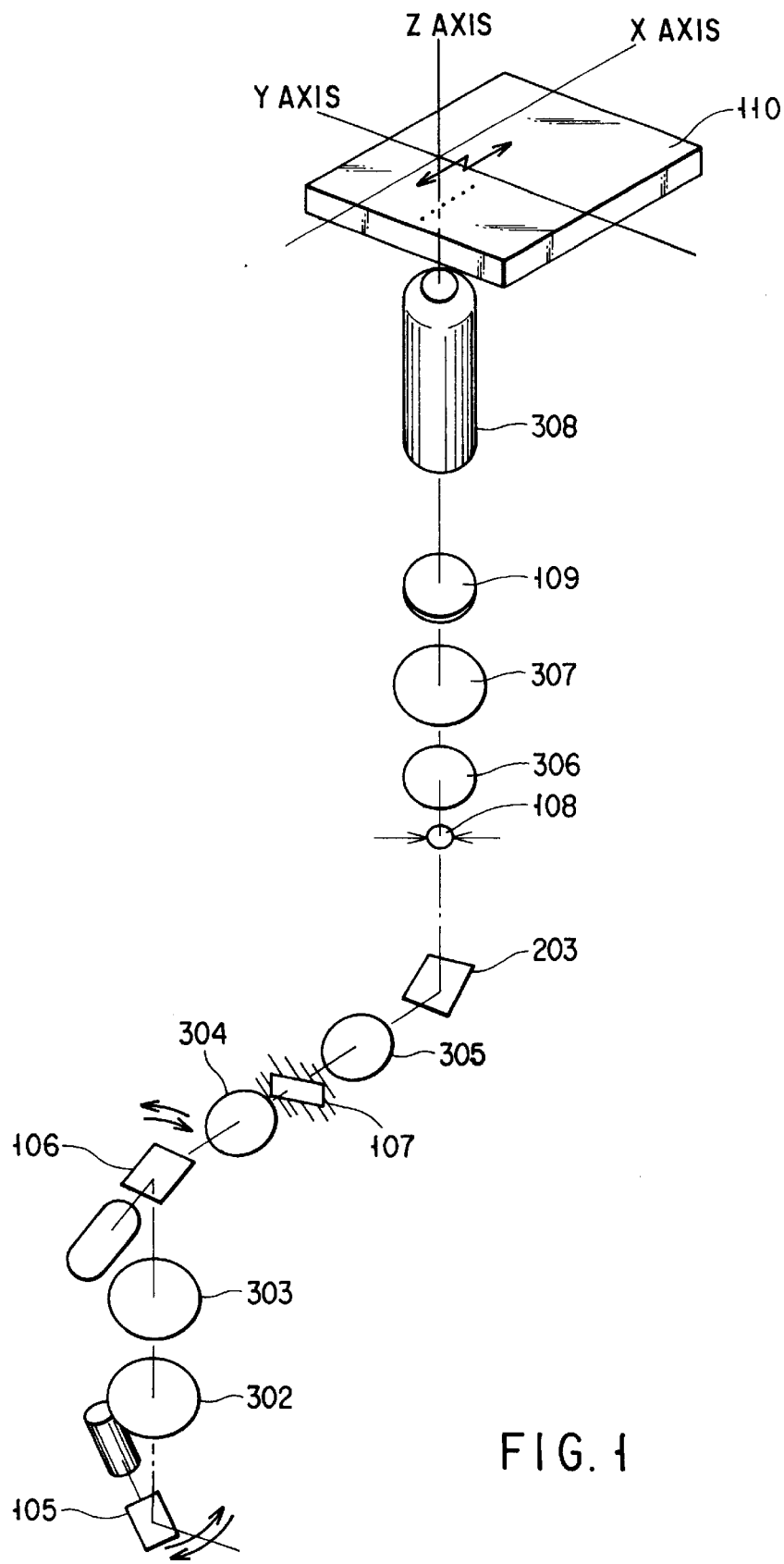
FIG. 1 is a view of a substrate side of a cofocal multi-beam scanning optical system in an optical substrate inspection apparatus according to a first embodiment of the present invention.
Figure 2:
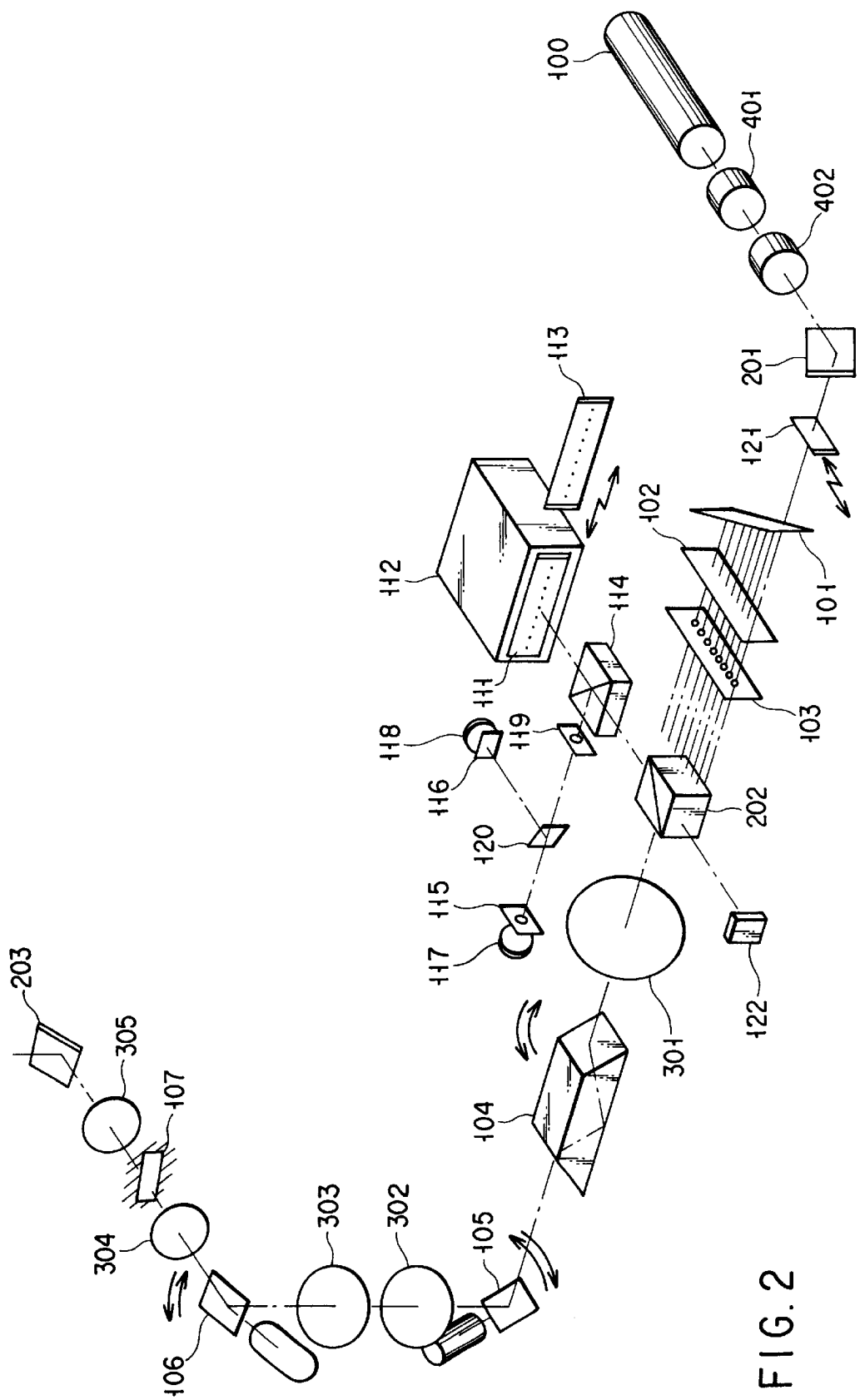
FIG. 2 is a view of a light source side of the cofocal multi-beam scanning optical system in the optical substrate inspection apparatus according to the first embodiment.
Figure 3:
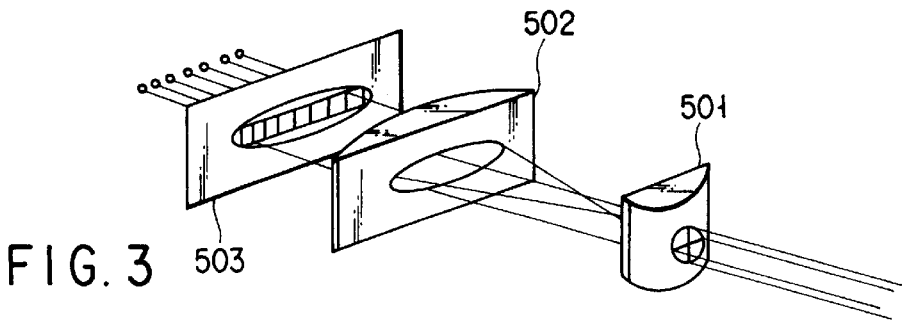
FIG. 3 is a view showing an optical system for generating multiple beams.

FIGS. 1 and 2 illustrate arrangements in the optical substrate inspection apparatus of the cofocal multi-beam type according to the first embodiment of the present invention.

A linear polarized laser light emitted from a laser tube 100 is passed through a high-speed shutter 401 and a shielding mechanism 402 and directed by a mirror 201 to a multi-beam generator 101. The multi-beam generator 101 may be of a filter type in which a plurality of beams are formed through a film arrangement. The multi-beam generator 101 splits a single beam into multiple beams which are then directed to a multi lens 102. The multi lens 102 may be a group of small lenses, a micro lens of ion-exchange type, or a zone plate of a phase type. The multiple beams produced from the multi-beam generator 101 and the multi lens 102 are converged.

Those converged beams may be generated by producing linear beams through cylindrical lenses 501 and 502 causing them to be incident on a multi lens 503. In terms of the efficiency and the variations of light intensity between the multiple beams, the use of the multi-beam generator 101 is preferable.

The converged beams (a multi-beam light) are focused on pin holes in the multi pin hole 103 which acts as an aperture regulating member. The multi pin hole 103 of the aperture regulating member is essential in the cofocal optical system and has a plurality of pin holes therein of which diameter is determined by a degree of diffraction calculated from the optical constant of the multi lens 102. The multi-beam light from the multi pin hole 103 is passed through a polarized beam splitter 202 and transmitted to a lens 301. The multi-beam light has been linear polarized so that they can pass the polarized beam splitter 202 at optimum efficiency.

The multi-beam light passed through the polarized beam splitter 202 is then transmitted via a rotating prism 104 to a scanner mirror 105. The rotating prism 104 is adjustable for determining The angle of the multi-beam light to a substrate of interest The multi pin hole 103 and the scanner mirror 105 are arranged telecentric to each other by section of the lens 301. This allows the beams to be parallel to each other after the lens 301 and overlapped one after another on the scanner mirror 105.

The location of the scanner mirror 105 is conjugate to the location of an iris at an objective lens 308, which will be explained later in more detail, so that its telecentric relationship on the substrate is established. Two mirrors 105 and 106 are assembled to form a scanner for scanning along two axes, X-axis and Y-axis. The mirror 105 is provided for main scanning and the other 106 is for sub-scanning. In this embodiment, the scanner mirror 105 is of a resonance type of which action and effect will be explained later. Using the two axes, a limited area in a two-dimensional image can be read by scanning while the table remains stationary.

The multi-beam light reflected by the two scanner mirrors 105 and 106 is then directed through two lenses 304 and 305 and a mirror 203 by which the conjugate location of the iris falls on a position denoted by 108 (an aperture stop). The numerical aperture NA on the substrate can thus be varied by the aperture stop 108 at the conjugate location of the iris controlling the flux of the multi-beam light. The aperture stop 108 may be substituted by a zone type which further contributes to the improvement of the resolution. The multi-beam light passed through the aperture stop 108 is transmitted via lenses 306 and 307, a $\lambda/4$ plate 109, and an objective lens 308 and focused on the substrate 110 to develop a row of beam spots spaced at equal intervals.

The multi-beam light released from the objective lens 308 is telecentric on the substrate and its reflection over the substrate 110 returns back along the same path hence passing the two scanner mirrors 105 and 106 in the opposite direction. Therefore, the X-axis polarized conditions of the multi-beam light are canceled by the Y-axis scanner mirror 106 and the X-axis scanner mirror 105 respectively. Accordingly, the multi-beam light is turned to its stationary state identical to the initial condition. The multi-beam light is further returned to the rotating prism 104 of which angular movement has been initialized and enters the polarized beam splitter 202.

The polarization of the laser beam is now explained. The beam emitted from the laser source is linear polarized and before entering the objective lens 308, is turned to a circular polarized state by the $\lambda/4$ plate 109. The reflection of the beam is then passed again through the $\lambda/4$ plate 109 where its polarization rotates 90 degrees and directed to the polarized beam splitter 202. Accordingly, the reflection of the multi-beam light is reflected on the polarized beam splitter 202 and hence directed to a multi pin hole 111 having a succession of apertures. The reflection of the beam converged by the multi pin hole 111 is given to a detector assembly 112 where a change in the signal amount of each beam is detected.

The polarization state is utilized in the optical system of the embodiment for the purpose of increasing the efficiency of the amount of light as well as preventing any reflection of the beam from turning to a noise component at the detector assembly. The multi pin hole 111 is similar in the construction to the multi pin hole 102 and has a succession of pin holes of a very small diameter therein which are essential for the cofocal optical system. The multi pin hole 111 can be replaced with another multi pin hole 113 of a different diameter.

The optical system having the above mentioned arrangement allows the multi-beam light to be a group of stationary fluxes on the detectors which can scan along the X axis and the Y axis separately. As the system provides a cofocal property, it incorporates a multi-beam cofocal inspection optical system.

Although it is easily planned for minimizing the time for inspection to scan the substrate with multiple beams simultaneously, the scanning with the multiple beams is a troublesome task. The multiple beams produced by the multi-beam generator 101 are incident on the multi pin hole 103 as there are spaced at equal intervals as shown in FIG. 2. In this embodiment, the multiple beams are produced from a single laser beam and have to be spaced from each other by a distance enough to prevent interference. If interference occurs, the measurement of each beam on the detector will be impaired in the independency hence causing the optical system to divert from its ideal lens dedicated performance. Also, the spacing the multiple beams from each other provides ease of the optical control of each beam at any point of the optical system.

Figure 4A:
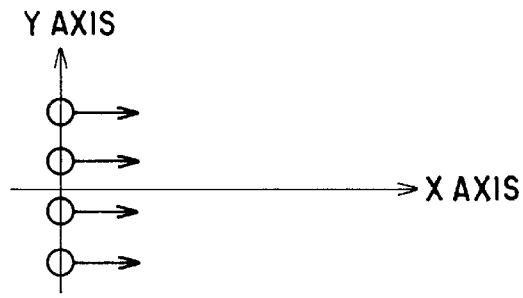
FIGS. 4A and 4B are diagrams showing a multi-beam scanning action.

However, when the optical alignment of the multiple beams spaced from each other is vertical to the main scanning direction as shown in FIG. 4A, it will be difficult to scan throughout the substrate. As apparent from FIG. 4A, there is generated a gap between any two adjacent beams where the inspection is not covered.

Figure 4B:
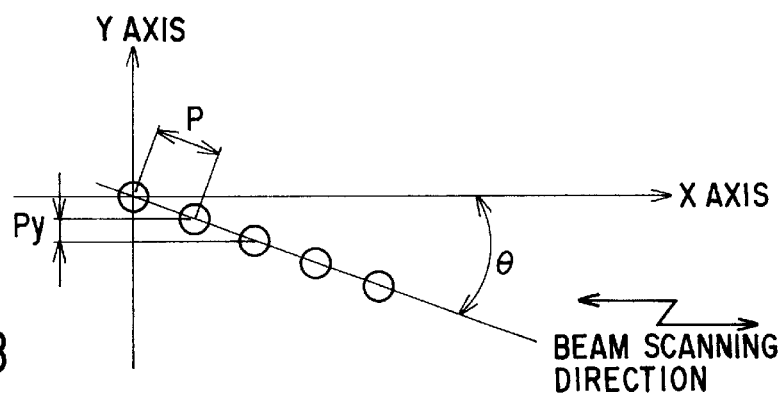
Figure 5:
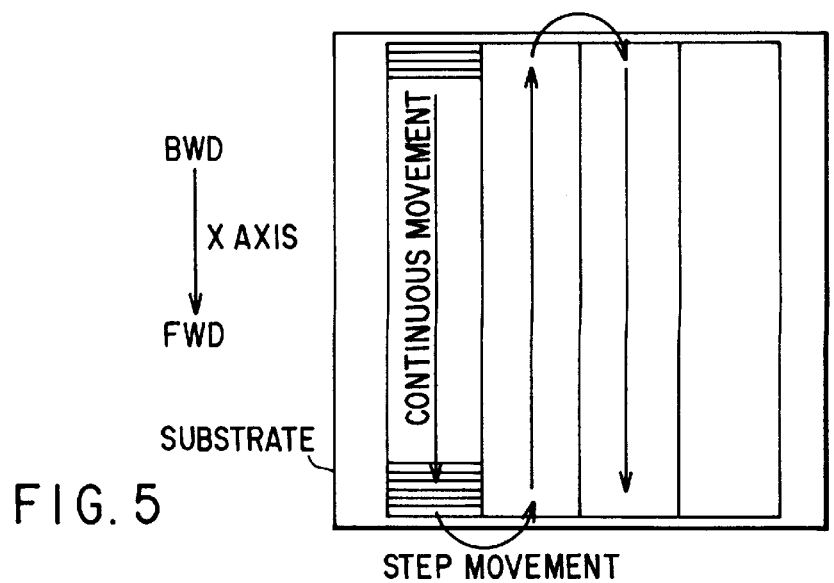
FIG. 5 is a diagram explaining an ideal table scanning action.

For compensation, the alignment of the multiple beams is arranged at an angle to the main scanning direction or the X axis as best shown in FIG. 4B. This allows the multiple beams to be aligned as closely as possible and scan the substrate without creating the gaps. Accordingly, the multi-beam scanning without generating uninspected areas can be achieved. Also, the illumination spots of the multiple beams do not overlap one another and their independency will be maintained throughout the optical system thus creating no interference on the detector.

The rotating prism 104 is designed for controlling The angle between the main scanning direction (the X axis) and the optical alignment of the multiple beams, as described below. More particularly, assuming that the distance between two adjacent multiple beams is P, The angle between the main scanning direction and the optical alignment of the multiple beams is θ, the diameter of the beam fallen on the substrate is a, and the diameter of the aperture of the multi pin hole 111 is a', the pitch Py projected along the Y axis of the distance P is expressed by:

$$Py = P \cdot \sin \theta = a = a'/\beta \tag{1}$$

where β represents the optical magnification between the multi pin hole 111 and the substrate 110. The angle θ between the main scanning direction (the X axis) and the multiple beams can easily be obtained by calculating the diameter a' of the aperture in the multi pin hole 111, the beam distance P, and the optical magnification b.

When the inspection at a higher speed is desired with a lower rate of the sensitivity of measurement, the aperture diameter of the multi pin hole 111 is increased. This can be implemented by increasing. The angle of movement of the rotating prism 104. Correspondingly, the aperture diameter of the multi pin hole 111 also has to be increased. When the sensitivity of measurement is increased to as a higher level as possible in the optical system, the aperture diameter of the multi pin hole 111 is decreased to a minimum close to the diffraction and a corresponding degree of The angle θ is determined by controlling the rotating prism 104.

The calculation of an actual optical constant in the optical system shown in FIGS. 1 and 2 follows. It is assumed that the wavelength of the beams used for the inspection is 351 nm and the numerical aperture of the objective lens is 0.75. The diameter D of the beam on the substrate is thus expressed by:

$$D = 1.22 \lambda / \text{numerical aperture NA} \tag{2}$$

Then, 0.57 μm is given. This section that the distance P should be more than 1 μm.

In fact, the distance P is 10 μm more or less at best due to the performance of the multi-beam generator 101. If the beam spot diameter a on the substrate is 0.2 μm, the aperture diameter a' of the multi pin hole 111 is calculated from a β. Using a=0.2 μm and P=10 μm, The angle θ is 1.15° from the equation (1). Provided that the multiple beams are not interfered by each other, a set of degrees of The angle θ are calculated from different values of the distance P and the spot diameter a (which is designated as an inspection mode in this embodiment) as listed in the following table.

Relation between the distance, the inspection mode, and The angle

| Inspection mode; 0.05 μm | | Inspection mode; 0.1 μm | | Inspection mode; 0.2 μm | |
|---|---|---|---|---|---|
| p (μm) | θ (degree) | p (μm) | θ (degree) | p (μm) | θ (degree) |
| 2 | 1.43 | 2 | 2.87 | 2 | 5.47 |
| 5 | 0.57 | 5 | 1.15 | 5 | 2.29 |
| 10 | 0.28 | 10 | 0.57 | 10 | 1.15 |

As apparent from the table, The angle θ is preferably 5 degrees or less in actual operations. As understood, the inspection with the multi-beam optical system of the embodiment can be conducted without trouble through spacing the multiple beams from each other by the distance P to produce no interference and controlling the rotating prism 104 to determine a optimum degree of The angle of the optical alignment of the multiple beams in response to the aperture diameter of the multi pin hole 111 loaded just before starting the inspection.

In addition to the rotating movement, it is necessary to set the traveling of the table at a right angle to the main scanning direction. This may be implemented by providing a known mechanism at an appropriate location in the optical system for rotating first a multi-beam scanner (along the X axis) and second a multi-beam scanner (along the Y axis) at once. Such a known mechanism is selected from various conventional techniques without difficulty.

The traveling speed v of the table in relation to the inspection mode is calculated from the following equation (3) while the aperture diameter a' of the multi pin hole 111 and the diameter a of the beam spot on the substrate are determined with the optical magnification β.

$$v = \text{numerical aperture } NAf \tag{3}$$

where n is the number of fluxes and f is the scanning frequency.

As explained above, the diameter of the beam spot on the substrate 110 is determined by the numerical aperture of the objective lens 308 and the wavelength of the beam used. Also, the traveling speed of the table and the sensitivity of measurement in the inspection can be set by changing the aperture diameter of the multi pin hole 111 disposed before the detector assembly 112. A desirable combination of the beam scanning, the table speed, and the rotation of the rotating prism 104 is thus essential.

The above equations are intended to provide preferred settings. Minimum discrepancy from the settings calculated from the equations may be allowed. In actual, while the settings have been determined through experiments and stored in a memory device, corresponding ones are selected and read from the memory device to complete the desired inspection mode.

This embodiment employs the cofocal optical system for providing ideal lens system conditions, wherein the multiple beams are scanned over the substrate or object to be inspected to read data of a pattern on the object. For the purpose, the beams of the cofocal optical system are scanned throughout the object while they have to remain stationary on the detectors. Accordingly, a optical double pass technique is used in which the beams pass the scanner mirror in both the forward and backward direction. Also, the scanner and the detector are used for scanning and detecting a signal, in which the object is scanned with a plurality of the scanning beams to avoid the decrease of the scanning speed which results from minimizing the scanning frequency in order to eliminate substantial requirements on the detector assembly including increase of the response speed and of the beam intensity.

The optical detector assembly 112 shown in FIG. 2 is designed for measuring a reference amount of the scanning beams. The reference amount of the incident beams is detected by measuring one of the multiple beams or a leak component from the polarized beam splitter 202. A variable signal of the reference intensity can be used for correcting the gain of an amplifier of each detector in the detector assembly 112. This technique permits compensation for changes in the amount of the laser beams. Also, a neutral density (ND) filter 121 is provided as a beam intensity adjusting filter for preventing saturation in the detector assembly 112 and can be inserted into the optical system when desired as shown. It is preferable to dispose a rotating prism 107 between the two lenses 304 and 305 for fine adjustment along the beam scanning direction.

The relation between the table traveling and the scanning direction is now explained. The most efficient movements of the table traveling may include a continuous movement in the forward direction FWD along the X axis, a step movement in the forward direction FWD along the Y axis, a continuous movement in the backward direction BWD along the X axis, and a step movement in the backward direction BWD along the Y axis. More particularly, the subscanning action of the table consists of FWD/BWD alternate movements for scanning throughout the substrate and the table traveling will thus fall within the time of inspection except the step movements. When the high speed scanning is desired, the stoke of scanning can be increased.

For improving the throughput, a scanner of polygon mirror type may be used in which the scanning with a beam is limited to in one direction. However, such a scanner can hardly cooperate with the above table traveling hence failing to improve the throughput.

The relation between the multi-beam scanning and table scanning or between the main scanning and the subscanning is explained referring to FIGS. 6A to 6F. FIGS. 6A to 6C illustrate the multi-beam scanning over the substrate with the table traveling in the FWD direction. It is assumed that the FWD direction of the subscanning is upward and the FWD direction of the main scanning is rightward throughout the figures. While the multiple beams are scanned along the scanning lines, the scanned area is apparently moved towards the upper of the figures. For inspecting throughout the scanned area which moves upwards, the multiple beams are set at a scanning angle α to the subscanning direction which is determined by the number of the beams, the diameter of the beam spot on the substrate calculated from the aperture diameter of the multi pin hole and the optical magnification, the stroke of the main scanning, the traveling speed of the table, and the scanning frequency of the main scanning and then scanned so that a pattern scanned area of the substrate scanned by the multiple beams is connected to the preceding scanned area along the main scanning direction.

It is now assumed that the subscanning is shifted to the BWD direction. In the optical system using the scanner of e.g. polygon mirror type where the scanning direction of the beams is limited to in one direction, the main scanning is in the FWD direction. In this case, The angle θ of the pattern scanned area is varied as shown in FIGS. 6D to 6F hence altering the shape of the pattern scanned area. As the result, the position of observation on the substrate in the main scanning will be changed by the subscanning action. Accordingly, the shift of the subscanning to an opposite direction will yield a different scanned image.

The above problem is however eliminated by using the scanner of resonance type in the multi-beam scanning optical system where the scanning of the beams is made in both the FWD and BWD directions. FIGS. 7A to 7F illustrate the scanning with the resonance type scanner. When the subscanning is in the FWD direction, the action is identical to that shown in FIGS. 6A to 6c, as shown in FIGS. 7A to 7C. In case that the subscanning is shifted to the BWD direction, a corresponding shift of the main scanning to the BWD direction allows the scanning lines and the scanning direction to substantially match the main scanning direction as shown in FIGS. 7D to 7F. Accordingly, the scanning angle and the scanning action will be aligned with the subscanning direction.

More specifically, The angle θ of the pattern scanned area is not changed in both the FWD and BWD subscanning actions as well as the shape of the pattern scanned area remains intact. Since the position of observation on the substrate is stationary regardless of the subscanning direction, a scanned image reproduced for the inspection is identical when the subscanning is made in an opposite direction.

The scanner of the resonance type for implementing the present invention is feasible using a galvanomirror, a resonance mirror, an acousto-optic deflector (AOD), or the like. The resonance type scanner is operable at a high speed but its scanning width is typically small. This may make it difficult to increase the operating speed by increasing the scanning stroke as compared with the polygon mirror where the beam scanning is limited to in one direction. However, The advantage of the polygon mirror is simulated by using a plurality of the scanning beams for the multi-beam scanning instead of increasing the scanning stroke. In addition, down time in the table movement is significantly minimized as descried above and a higher operating speed of the inspection apparatus of the embodiment will be guaranteed.

The system arrangement according to the present invention is novel because a combination of the multi-beam scanning and the resonance scanner provides a higher ability of improving the throughput than any conventional system.

In the embodiment, the cofocal optical system is used for implementing an ideal lens system where an object to be inspected is scanned by laser beams to gain data of a pattern on the object. While the scanning with the beams is carried out over the object, the beam have to be stationary on the detectors in the cofocal optical system. For the purpose, the optical double pass arrangement is employed where the beams pass the scanner mirror two times in the forward and backward directions.

Also, in the technique for producing a signal by scanning and detecting it in the detector, secondary requirements including the increase of the response speed and the beam intensity at the detector are developed as the scanning frequency increases. For minimizing the scanning frequency and avoiding the subsequent decrease of the inspection speed, the multiple beams are used in the optical system. For further increasing the resolution, an intermittent illumination for the inspection is used in the embodiment. More specifically, the high-speed shutter 401 is disposed just after the laser source.

The high-speed shutter 401 is designed for passing and interrupting the laser beam at intervals of a given time or cycle and may be a mechanical shutter or an acousto-optic modulator (AOM). The location of the shutter may be changed along the optical path before the detector assembly with equal success.

The advantage of the shutter for passing and interrupting the laser beam at intervals of a given time or cycle is as follows. The detector of a higher sensibility receives different intensities of the input beam between continuous illumination and pulsed illumination. The amount of the pulsed beam can be sensed at a higher sensitivity than that of the continuous beam. As the amount of input light is regarded as a sum of received light per unit time, the short period of time can accept a more amount of the received light.

In the inspection, the substrate is scanned on the basis of a unit matrix of cells which are defined by the spot diameter of the scanning beam. Therefore, during the movement of the scanning beam from one cell to another no detection of the intensity is necessary at the detector. The intermittent illumination for the inspection permits the received beam by the detector to be increased in the absolute intensity and thus its S/N ratio to be improved. Accordingly, smaller signals indicative of minimal defects which are mixed in the noise and hardly identified by the conventional manner can be extracted.

When the laser beam from a laser source is significantly increased in the power and decreased in the wavelength, it may give damage to the substrate. The laser beam for scanning on the substrate is converged to as a small spot as its wavelength limitation and remains incident on the substrate while the inspection is paused. If the laser source is turned off frequently, more extra time for warming up the laser source is needed. For minimizing the down time during the inspection, the laser source is commonly kept turned on.

As the inspection is being paused, the laser beam falls on a particular region of the substrate which is held at one location on the table. When the region of the substrate has directly been exposed to the high amount of the laser beam for an extended duration of time, its pattern and itself may be heated and injured.

In the embodiment, the shielding mechanism 402 is provided after the high-speed shutter 401 for preventing the above trouble. The shielding mechanism 402 may be disposed at any location between the laser source and the substrate with equal success. Since the laser beam is blocked by the shielding mechanism 402 during the non-inspection time, it is prevented from giving damage to the substrate. The shielding mechanism 402 may be combined with the high-speed shutter 401 which is located between the laser source and the substrate. This will provide the increase of the S/N ratio and the prevention of the illumination injury with a single mechanism.

The automatic focusing mechanism provided in the optical system shown in FIGS. 1 and 2 is now explained. The automatic focusing mechanism is of a through-the-lens (TTL) type for selecting and measuring one of the reflected beams reflected by the substrate and received by the detectors to determine the focal point.

Referring to FIG. 2, a portion of the multi-beam light transmitted from the polarized beam splitter 202 to the detector assembly 112 is diverted to the left in the figure by a half mirror 114 disposed in front of the detector assembly 112. The multiple beams reflected on the half mirror 114 are directed to a filter 119 where one of the multiple beams is selected and transmitted to a half mirror 120. The half mirror 120 divides the beam into two components which are received by two detectors 117 and 118 respectively. Pin holes 115 and 116 of which aperture size is determined by the diffraction limitation are provided in front of the detectors 117 and 118 respectively so that they locate before and after the focal point (along the optical path).

Figure 8A:
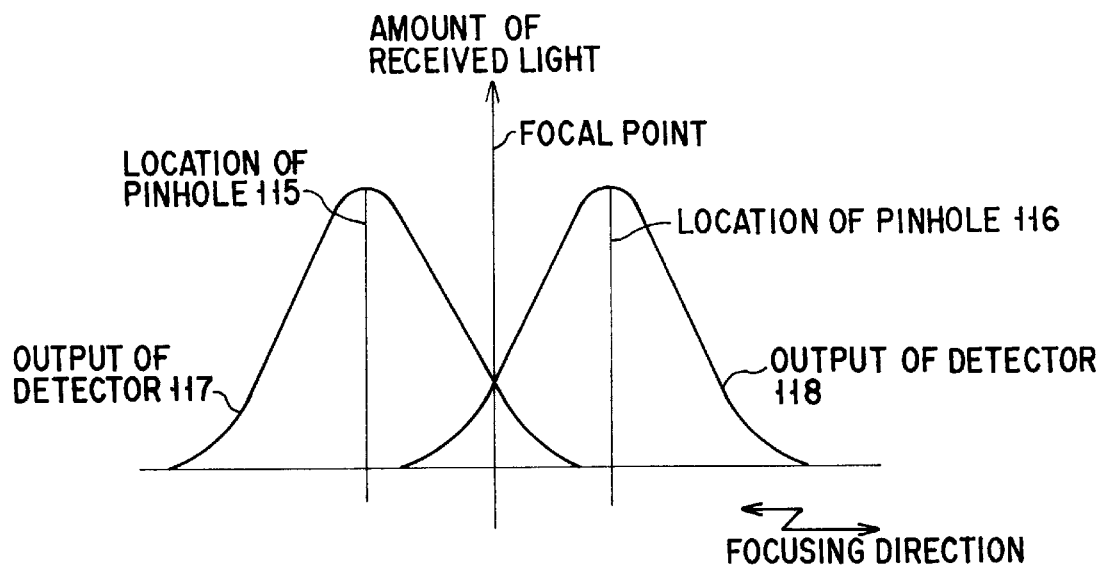
FIGS. 8A and 8B are diagrams explaining the principle of focusing.
Figure 8B:
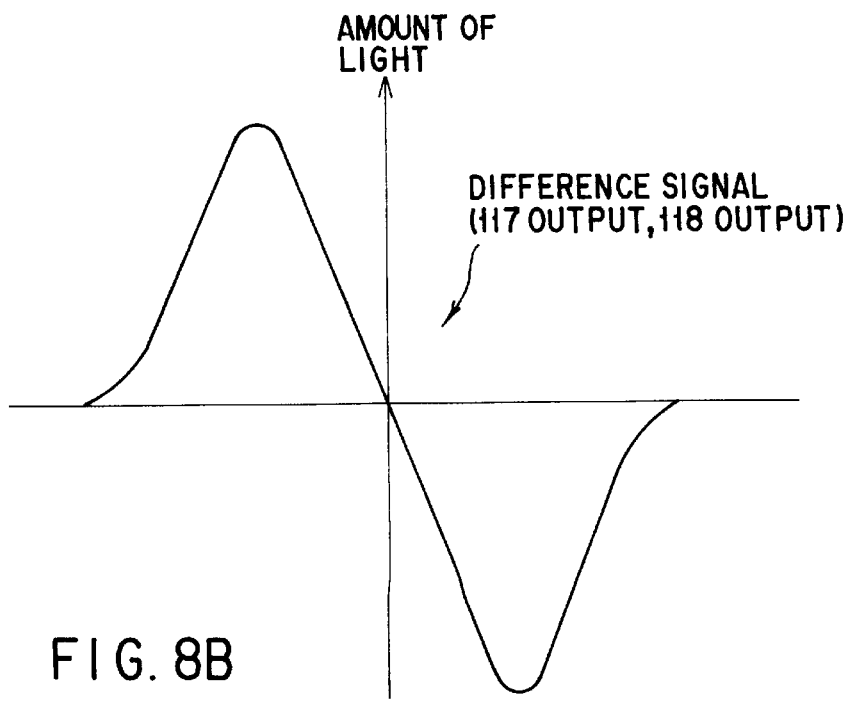

While the focal point on the substrate (along the Z axis) is varied, two signals of the intensity are detected by the detectors 117 and 118, as shown in FIG. 8A, which are peaked when the beams are focused to the focal points of the pin holes 115 and 116. A difference between the two signals of their respective detectors 117 and 118 is calculated by a circuit (not shown) and its signal is expressed along the Z direction as shown in FIG. 8B. The focal point on the substrate is hence determined from the zero-cross point of the difference signal. More particularly, The automatic focusing action is carried out by driving a table servo mechanism in the Z direction in accordance with the detector signals.

The automatic focusing mechanism in the embodiment is assembled in the optical system for the inspection and shares the laser beam used for the inspection to conduct an automatic focusing action, thus being not susceptible to any external interference resulting from environmental change. While the beam scanning with the scanner mirrors 105 and 106 is being performed, the multiple beams are stationary on the detectors which can thus detect accurate measurements. When the action of the scanner mirrors 105 and 106 has been canceled and the focal point detection is started, any focusing error or a deflection of the substrate will be identified. When the focal point detection is made during the beam scanning, an average of the focal point locations can be calculated within the scanned area of the substrate.

According to the embodiment of the present invention, the super resolution optical system is established where the resolution of a image of the pattern scanned is significantly enhanced and the detection signal indicative of a minimal defect is increased higher in the amplitude than that of any conventional optical system. Also, the multiple beams are employed without modifying the super resolution optical system, having no use of the integral illumination and the single beam scanning. This eliminates the decrease of the beam intensity and the signal response on the detectors, thus preventing the speed of the inspection from being declined. It is anticipated in the near future that the use of shorter wavelength laser beams is common. The optical system in the inspection apparatus of the embodiment will be compatible with such a new requirement.

The optical system of the embodiment includes the resonance type scanners arranged for scanning of the beams in both the FWD and BWD directions and thus permits the object or substrate to be scanned from one pattern scanned area to another with no space when the subscanning is shifted from the FWD direction to the BWD direction or vice versa. This contributes to the significant decrease of down time in the table traveling without increasing relevant mechanisms. In particular, the combination of the multi-beam scanning and the resonance type scanner is highly advantageous for increasing the throughput of the inspection apparatus. The high-speed shutter allows the absolute amount of the scanning beam to be increased, hence improving the S/N ratio of the detection signal. Accordingly, any small error signal mixed in the noise and hardly identified can be extracted with ease. Also, the shielding mechanism blocks the laser beam when the inspection is paused, thus preventing a physical damage to the object or substrate.

The pattern inspection apparatus of the present invention designed for overcoming the conventional drawbacks is not limited to the foregoing embodiment and changes and modifications on the optical components, their layout, and relevant accessories will be possible. For example, the scanner may be replaced by an acousto-optic device. The multi pin hole 103 used as the aperture adjusting member in the embodiment may be a solid body having physically slotted apertures therein or a glass mask. Change in the component structure and layout may be made without departing from the scope of the present invention.

(Second Embodiment)

Figure 9:
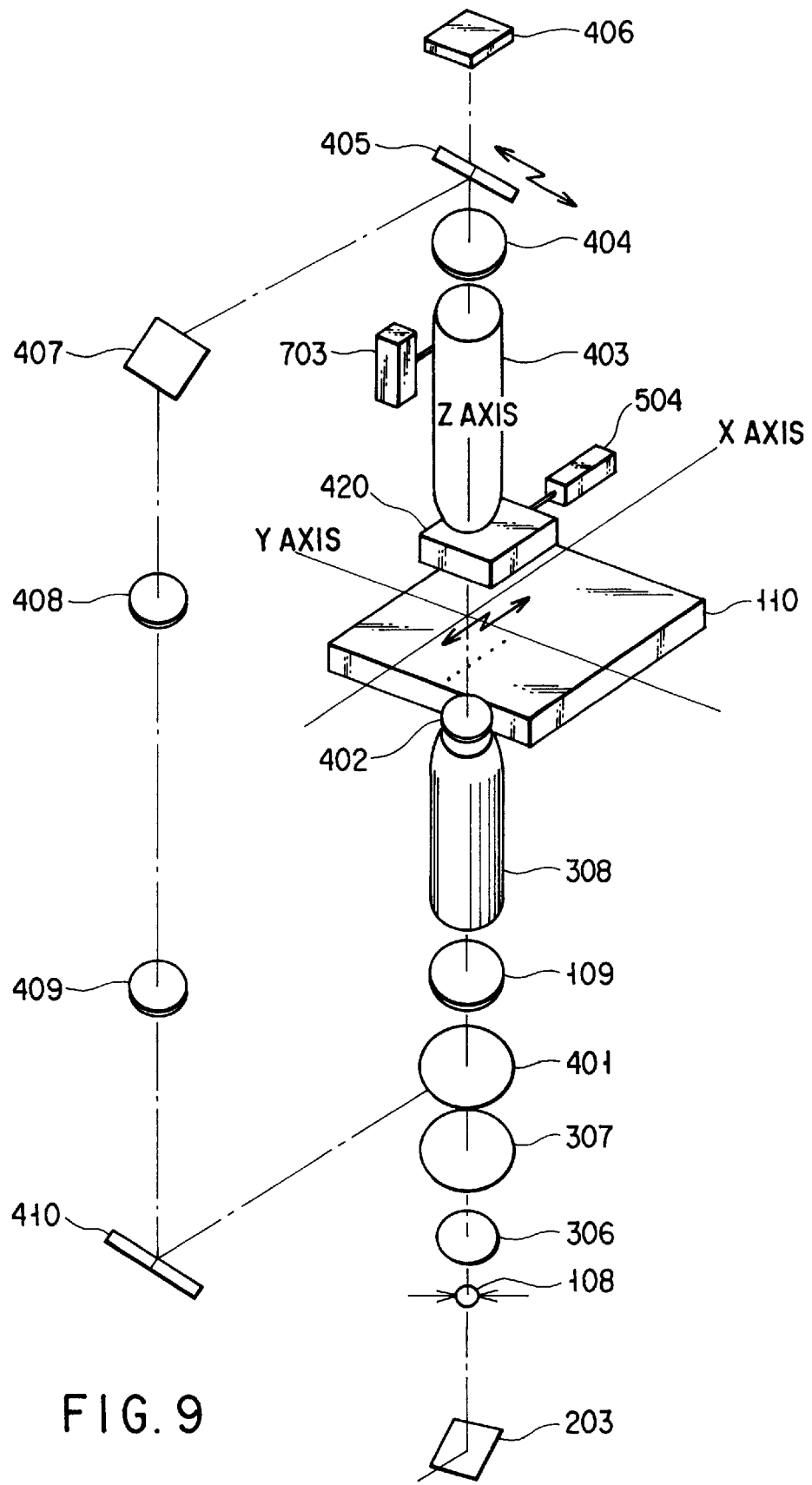
FIG. 9 is a view of a substrate side of a cofocal multi-beam scanning optical system in an optical substrate inspection apparatus according to a second embodiment of the present invention.

FIG. 9 illustrates a cofocal, multi-beam optical system in an optical substrate inspection apparatus according to the second embodiment of the present invention. The arrangement of components on the laser source side of a mirror 203 is identical to those shown in FIG. 2 and cited for the following description. Like components are denoted by like numerals as those shown in FIG. 1 and will be described in no more detail.

A linear polarized laser light emitted from a laser tube 100 is passed through a high-speed shutter 401 and a shielding mechanism 402 and directed by a mirror 201 to a multi-beam generator 101. The multi-beam generator 101 causes one single beam of the light to split into multiple beams which are then directed to a multi lens 102. The multiple beams (a multi-beam light) are converged and focused on the pin holes in a multi pin hole 103. The multi-beam light released from the multi pin hole 103 is passed through a polarized beam splitter 202 and directed to a lens 301.

The multi-beam light is then transmitted via a rotating prism 104 to a scanner mirror 105. The multi pin hole 103 and the scanner mirror 105 are arranged telecentric to each other by section of the lens 301. This allows the beams to be parallel to each other after the lens 301 and overlapped one another on the scanner mirror 105. The location of the scanner mirror 105 is conjugate to the location of an iris at an objective lens 308 so that its telecentric relationship on the substrate is established. Two mirrors 105 and 106 are assembled to form a scanner for scanning along two axes, X-axis and Y-axis. The mirror 105 is provided for main scanning and the other 106 is for sub-scanning.

The multi-beam light reflected by the two scanner mirrors 105 and 106 is then directed through two lenses 304 and 304 and a mirror 203 by which the conjugate location of the iris falls on a position denoted by 108 (an aperture stop). The numerical aperture NA on the substrate can thus be varied by the aperture stop 108 at the conjugate location of the iris controlling the flux of the multi-beam light. The aperture stop 108 may be substituted by a zone type which further contributes to the improvement of the resolution.

The multi-beam light passed through the aperture stop 108 is transmitted via lenses 306 and 307. The light runs through a mirror 410, lenses 409 and 408, mirrors 407 and 405, and a $\lambda/4$ plate 404 and after passing a condenser lens 403 and a substrate thickness compensating mechanism 420, falls on a substrate 110 to form a row of beam spots spaced at equal intervals. The multi-beam light released from the condenser lens 403 is telecentric on the substrate and after transmitting through the substrate 110, is directed to an objective lens 308 arranged telecentric to the substrate.

The multi-beam light passing through the substrate 110 and the objective lens 308 is directed through a $\lambda/4$ plate 109 and a polarized beam splitter 401 and returned to the original path before running in a backward direction to the two scanner mirrors 105 and 106. Accordingly, the Y-axis and X-axis polarized conditions of the multi-beam light are canceled by the Y-axis scanner mirror 106 and the X-axis scanner mirror 105 respectively and the multi-beam light is shifted back to its stationary state identical to the initial condition. The multi-beam light is further directed back to the rotating prism 104 which has been rotated back to its original state and returned to the polarized beam splitter 202.

The polarization of the laser light is now explained. The laser light emitted from the source is linear polarized and turned by the λ/4 plate 404 to a circular polarized condition before entering the condenser lens 403. As the multi-beam light has passed through the condenser lens 403, the substrate 110, and the objective lens 308, its polarization is rotated 90 degrees by the λ/4 plate 109 and shifted back to the linear polarized condition which is in turn directed to the polarized beam splitter 202. The multi-beam light transmitted through the substrate 110 is reflected by the polarized beam splitter 202 and directed to the multi pin hole 111. The multiple beams converged by the multi pin hole 111 are given to a detector assembly 112 where their signal intensity is measured.

It is easy to minimize the time for the inspection by scanning the substrate at a time with the multiple beams. However, the actual practice of multi-beam scanning is not a easy task. The second embodiment employs a cofocal optical system of a transmission type which can provide a higher level of the resolution and allows the multiple laser beams to be scanned over the substrate or object to read data of a pattern to be inspected at a higher sensitivity.

In the cofocal optical system, the multiple beams have to be accurately focused on the pattern on the substrate. Generally, the entire length of the optical path in the transmission type optical system unlike the reflection type is determined by considering the thickness of the substrate. While the lenses and prisms in the optical system are substantially fixed and unchanged, the substrate to be inspected is replaced one after another. In common, the substrates are not uniform in the type, the allowance, and the surface flatness. As variation in the thickness of the substrate entails change of the aberration, the cofocal optical system is hardly stabilized in the resolution of an inspection image. For that reason, the use of a transmission type, cofocal optical system in the substrate inspection apparatus or namely, a transmission type, multi-beam, cofocal optical system is very rare in the field.

The transmission type optical system of this embodiment includes a section for compensating the variation of the substrate thickness which is implemented as the substrate thickness compensating mechanism 420 provided on an illumination optical system side.

Figure 10:
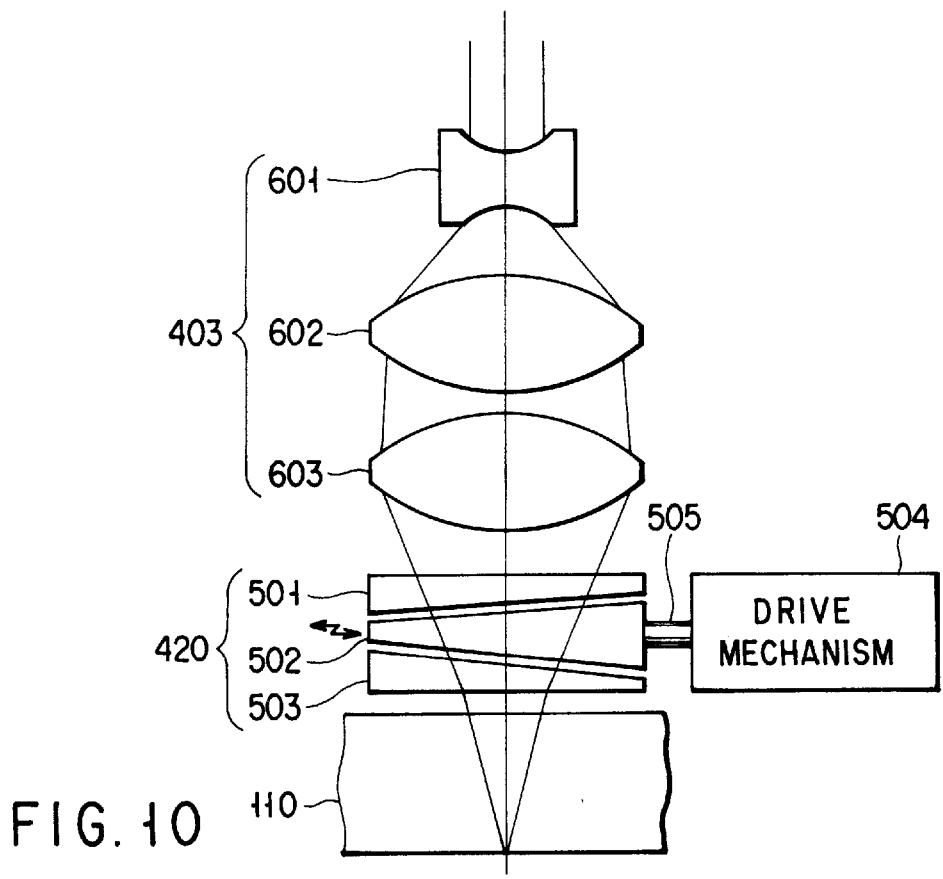
FIG. 10 is a schematic view of a substrate thickness compensating mechanism using prisms.

FIG. 10 is a schematic view of the substrate thickness compensating mechanism 420 using a group of prisms. The condenser lens 403 comprises a series of lenses 601, 602, and 603. The prisms 501, 502, and 503 of the substrate thickness compensating mechanism 420 are designed for adjusting the length of the optical path. With the prisms 501 and 503 being shifted to left and right in relation to the prism 502, the optical path can continuously be varied to a desired length. The varying the length of the optical path through the prisms can offset a change in the overall length of the optical path in the system which has been caused by a non-uniform thickness of the substrate.

The prism 502 is joined to a driving mechanism 504 which is responsive to a drive signal for shifting the prism 502 in relation to the other prisms 501 and 503. The length of the optical path can thus be adjusted continuously by changing the stroke of shift. Instead, the prisms 501 and 503 may be joined to the driving mechanism 504 for shifting motion in relation to the prism 502 with equal success. Moreover, the substrate thickness compensating action may automatically be carried out by section of a substrate thickness detector, not shown, for measuring the thickness of the substrate and a drive control circuit of the driving mechanism 504. In action, the thickness of the substrate, particularly at the current observing point, is measured with the substrate thickness detector and its signal is sent to the drive control circuit which then drives the driving mechanism 504.

The substrate thickness detector is preferably of a non-contact type, but for roughly measuring the thickness, a technique of directly contacting and measuring the back side of the substrate where the pattern is absent may be used. This is done by determining the location of both the front (pattern) and back sides of the substrate over the reference point and measuring a distance between the pattern side and the back side. The technique is well known and will be explained in no more detail. The non-contact detector may be selected from optical, overcurrent, ultrasonic, and other applicable types. Its application is identical to that of the contact type and will no more be explained.

With an optical type of the detector having a TTL optical system, the compensation can be conducted while the thickness of the substrate is being measured at real time. In that case, the measurement of the thickness may be carried out using either one of the multiple beams of the embodiment or another detecting beam which is different in the wavelength or the polarization from the multi-beam light. Anyway, the drive control circuit upon receiving a detection signal indicative of the thickness of the substrate from the substrate thickness detector can identify the location of and control the action of the driving mechanism 504.

Figure 11:
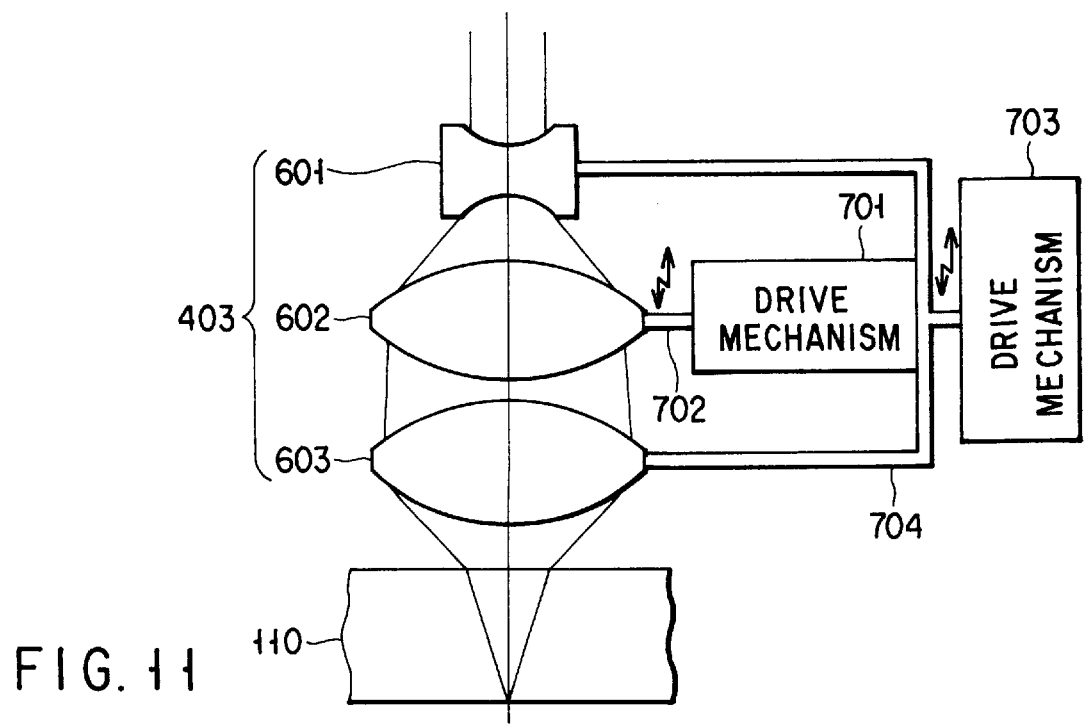
FIG. 11 is a schematic view of a substrate thickness compensating mechanism using condenser lenses.

Further, the substrate thickness compensating mechanism 420 may be implemented using a condenser lens assembly. FIG. 11 schematically shows such a substrate thickness compensating mechanism with the condenser lens assembly. The condenser lens assembly 403 is substantially similar to that shown in FIG. 10. In particular, a lens 602 of the condenser lens assembly is joined by a driving shaft 702 to a driving mechanism 701 for moving upward and downward. The other lenses 601 and 603 are joined together with the driving mechanism 701 by a driving shaft 704 to a driving mechanism 703 for moving upward and downward.

The driving mechanism 703 is a common focusing device for focusing the beam on the pattern on the substrate of a given thickness and when the thickness is varied, shifting the lens 602 upward and downward to correct the aberration. The driving mechanisms 701 and 703 both are responsive to corresponding drive signals and can be controlled for their action. Similarly, the substrate thickness compensation may automatically be conducted with a drive control circuit of the driving mechanisms 701 and 703 and a substrate thickness detector not shown.

The measurement of the thickness of the substrate is identical to that described above and will be explained in no more detail. The thickness of the substrate is used in the form of a detection signal for actuating the driving mechanisms 701 and 703 in a combination. Accordingly, the drive control circuit upon receiving the detection signal indicative of the thickness of the substrate from the substrate thickness detector can determine the location of and control the action of the driving mechanisms 701 and 703.

The automatic control of the substrate thickness compensating mechanism 420 may be carried out with no use of the substrate thickness detector. Instead, the detector assembly 112 is used. Through scanning the driving mechanism 504 or 701 so that the detection signals in the detector assembly 112 are maximum, the prisms or lenses can be moved to their optimum location. This will also achieve The automatic substrate thickness compensation of the embodiment with equal success.

The same effect may further be obtained by a combination of the prism movement and the condenser lens movement. In the optical system of the second embodiment, this combination is employed as a two-step substrate thickness compensating mechanism for carrying out rough adjustment with the prisms and fine adjustment with the condenser lens, hence allowing a wider range of variations of the substrate thickness. The substrate thickness compensation can, of course, be conducted automatically by a combination of the substrate thickness detector, the prism driving mechanism, the condenser lens driving mechanism, and the movable lens driving mechanism which are provided in the optical system but not illustrated.

With the substrate thickness compensating mechanism, the optical aberration which varies depending largely on the thickness of the substrate can be minimized by comparing the difference in the thickness over the type, the allowance, and the flatness of the substrate. Accordingly, the substrate inspection apparatus utilizes the transmission type cofocal optical system as one feature of the prevent invention for increasing the resolution of an inspection image and, as the other feature, includes the multi-beam scanning. As the result, the multi-beam scanning, transmission cofocal optical type of the substrate inspection apparatus is realized as capable of conducting the inspection at a higher speed than any conventional apparatus.

Accordingly to the second embodiment of the present invention, the aberration variation caused by the change in the thickness of the substrate is minimized in the cofocal optical system of light transmission type. This will provide the same advantage as of the first embodiment and also guarantee a higher sensitivity of the substrate inspection apparatus for detecting a minimal defect or dust on the pattern of a light transmission type which may be critical to the quality of mask and reticle products. Also, the multi-beam scanning optical system allows the throughput duration for the inspection to be minimized.

(Third Embodiment)

Figure 12:
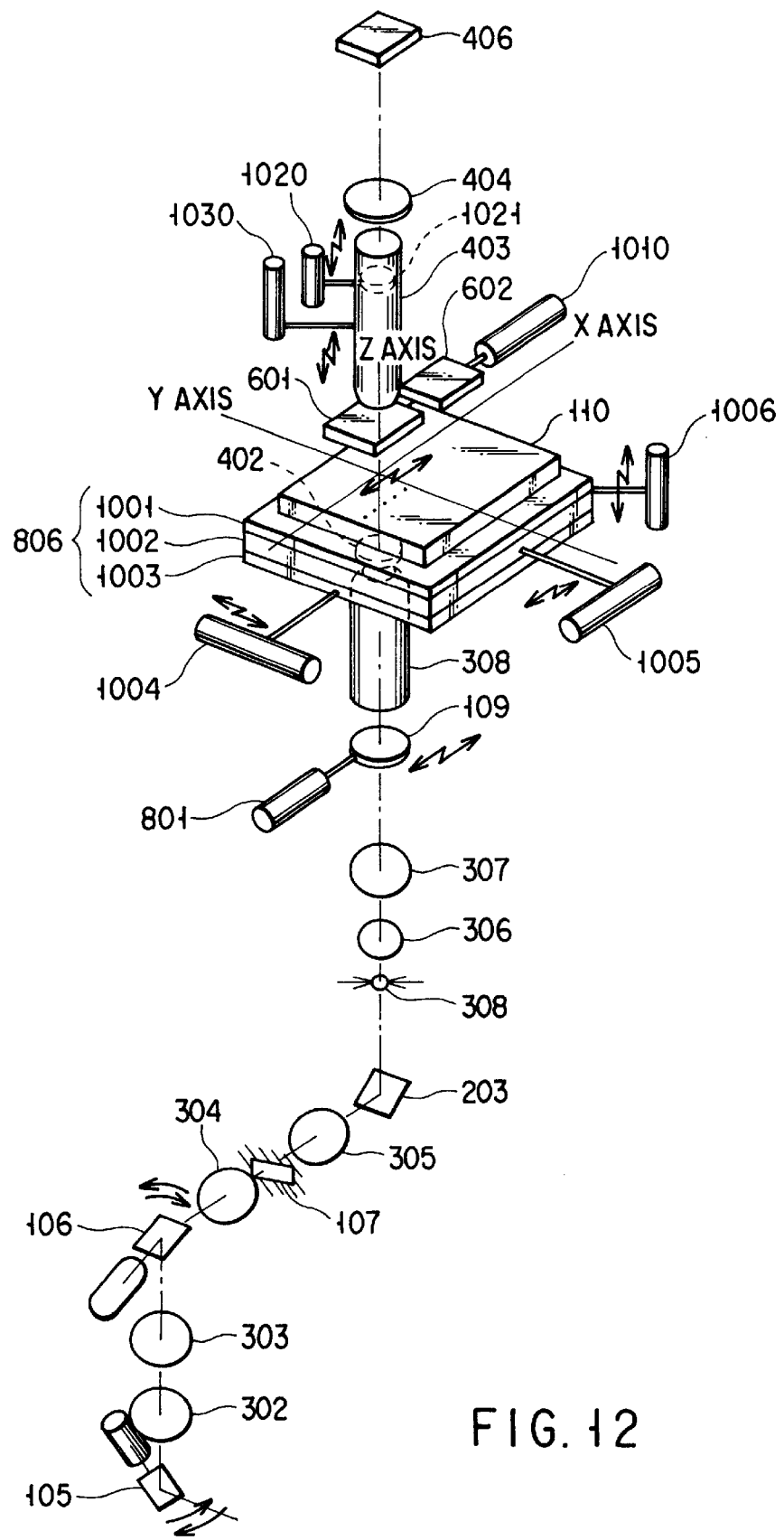
FIG. 12 is a view of a substrate side of a cofocal multi-beam scanning optical system in an optical substrate inspection apparatus according to a third embodiment of the present invention.
Figure 13:
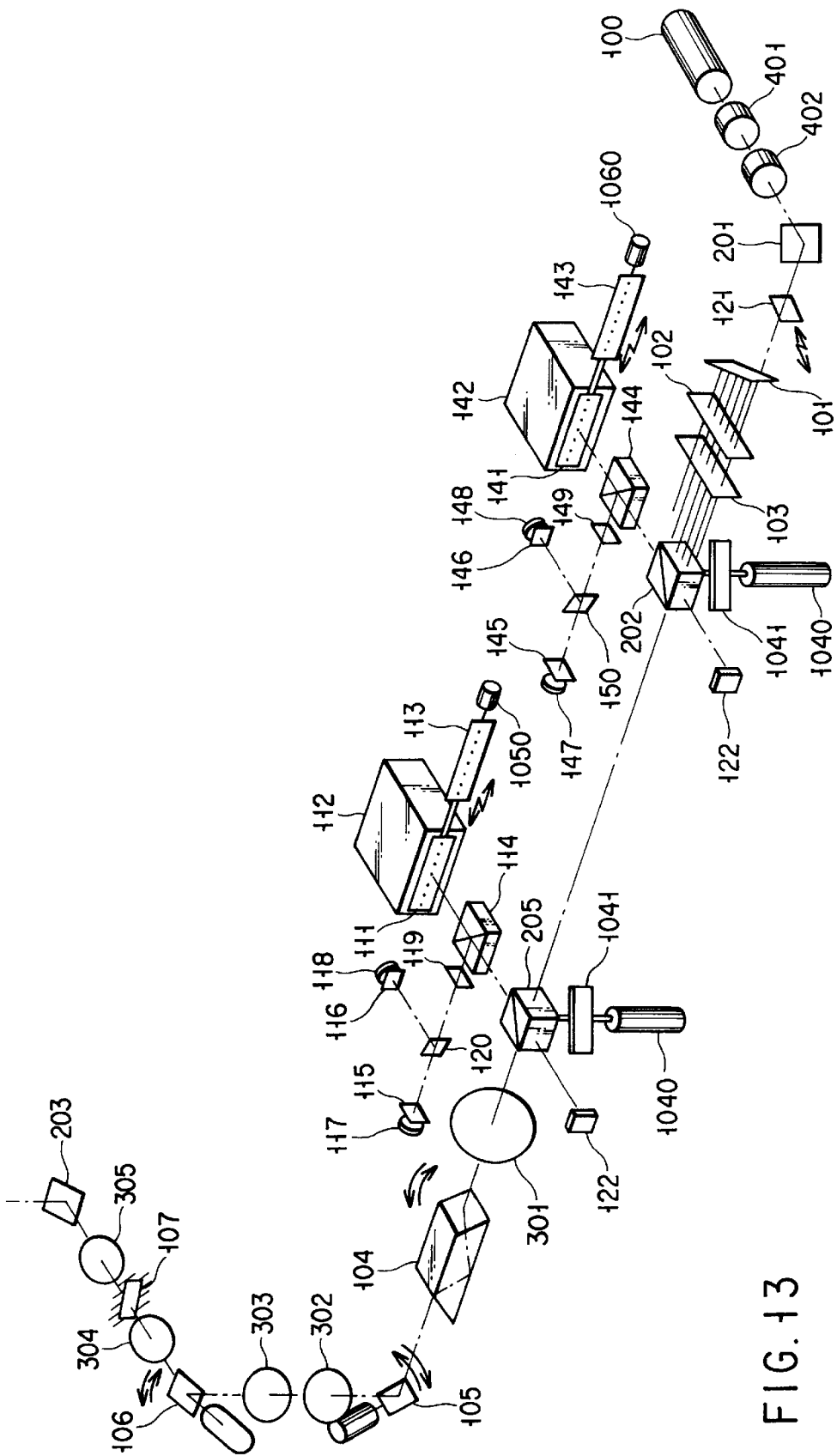
FIG. 13 is a view of a light source side of the cofocal multi-beam scanning optical system in the optical substrate inspection apparatus according to the third embodiment.

FIGS. 12 and 13 illustrate a cofocal, multi-beam optical system in an optical substrate inspection apparatus according to the third embodiment of the present invention.

The optical substrate inspection apparatus of the third embodiment is characterized by a light reflection and transmission type cofocal optical system as compared with the transmission type cofocal optical system of the first and second embodiment. Hence, like components are denoted by like numerals as those shown in FIGS. 1 and 2 and will be described in no more detail. A reflection type cofocal optical system region of the apparatus and its relevant components will chiefly be explained.

Similar to the previous embodiments shown in FIGS. 1 and 2, a linear polarized laser light emitted from a laser tube 100 is passed through a high-speed shutter 401 and a shielding mechanism 402 and directed by a mirror 201 to a multi-beam generator 101. The multi-beam generator 101 causes one single beam of the light to split into multiple beams which are then directed to a multi lens 102. The multiple beams are generated and converged by the multi-beam generator 101 and the multi lens 102.

The multiple beams (a multi-beam light) converged are then focused on the pin holes in a multi pin hole 103. The multi-beam light released from the multi pin hole 103 is passed through polarized beam splitters 202 and 205 and directed to a lens 301. The multi-beam light passing through the polarized beam splitters 202 and 205 and the lens 301 is then transmitted via a rotating prism 104 to a scanner mirror 105.

The multi-beam light reflected on the scanner mirror 105 and a scanner mirror 106 are passed through lenses 304 and 305 and a mirror 203 and conjugate to the location of an iris denoted by 108 (an aperture stop). The numerical aperture NA on the substrate can thus be varied by the aperture stop 108 at the conjugate location of the iris controlling the flux of the multi-beam light. The multi-beam light passed through the aperture stop 108 is transmitted via lenses 306 and 307, a $\lambda/4$ plate 409, and objective lens 308 and falls on a substrate 110 to form a row of beam spots spaced at equal intervals.

The multi-beam light released from the objective lens 308 is telecentric on the substrate. Then, the multi-beam light is separated into a transmission light for transmitting across the substrate 110 and a reflection light for reflecting on the substrate 110. The transmission light passed across the substrate 110 is directed to a substrate thickness compensating plate 601 where it is turned to a telecentric form on the substrate and then given to an objective lens 403 joined with a substrate thickness compensating mechanism. The multi-beam light passing the objective lens 403 is passed through a $\lambda/4$ plate 404 and directed to a mirror 406. The multi-beam light is then reflected by the mirror 406 and returned to the original path before running back to the two scanner mirrors 105 and 106. Accordingly, the Y-axis and X-axis polarized conditions of each of the transmission and reflection multi-beam lights are canceled by the Y-axis scanner mirror 106 and the X-axis scanner mirror 105 respectively and the multi-beam light is shifted back to its stationary state identical to the initial condition. The multi-beam light is further directed back to the rotating prism 104 which has been rotated back to its original state and returned to the polarized beam splitter 205.

The polarization of the laser light is now explained. The transmission light is linear polarized as emitted from the laser source and after passing the objective lens 403, turned by the $\lambda/4$ plate 404 to a circular polarized condition before entering the mirror 406. As the multi-beam light has been reflected by the mirror 406, its polarization is rotated 90 degrees by the $\lambda/4$ plate 404 and shifted back to the linear polarized condition which is then passed across the substrate 110 and directed to the polarized beam splitter 205. The reflection light is linear polarized as emitted from the laser source and remains not optically rotated until, after reflected by the substrate 110, it reaches the polarized beam splitter 205 via the objective lens 308. In other words, the reflection light falls on the polarized beam splitter 205 in its linear polarized state.

The transmission multi-beam light transmitted through the substrate 110 is reflected by the polarized beam splitter 205 and directed to the multi pin hole 111. The multiple beams converged by the multi pin hole 111 are given to a detector assembly 112 where their signal intensity is measured. The reflection multi-beam light passing the polarized beam splitter 205 is reflected by the polarized beam splitter 202 and directed to a multi pin hole 141. The reflection multiple beams are then converged by the multi pin hole 141 and directed to a detector assembly 142 where their signal intensity is measured.

The polarized beam is used in the optical system because its reflection created on a midway in the optical system is received as not a noise by the detector assembly as well as its intensity efficiency is improved. The multi pin holes 111 and 141 like the multi pin hole 102 have a succession of pin holes of a small diameter therein for providing the cofocal characteristics in the optical system of this embodiment.

According to the optical system of this embodiment, the multiple beams can be scanned along the X axis and the Y axis respectively and remain stationary on the detector assembly when having been transmitted through and reflected by the substrate. Also, the reflection light and the transmission light can dependently be measured by their respective detector assemblies in both the transmission and reflection cofocal optical systems. More specifically, the multi-beam scanning, transmission and reflection type cofocal optical system is established.

The substrate 110 is loaded on a substrate holding mechanism (a table) 806 which includes a Z-axis substrate holding mechanism 1001 driven by a driving mechanism 1006 in a direction parallel to the optical path. The substrate holding mechanism 806 is placed on an X stage 1002 driven by a driving mechanism 1005 and a Y stage driven by a driving mechanism 1004 so that the substrate 110 can be moved in the X and Y directions for desired positioning. More specifically, the substrate holding mechanism 806 is supported by pneumatic bearings for allowing the precise control action of each driving mechanism.

The $\lambda/4$ plate 109 is moved by a driving mechanism 801 to and from the optical path. The substrate thickness compensating plate 601 can be replaced with another substrate thickness compensating plate 602 which is different in the thickness from 601. A particular lens 1021 of the objective lens 403 is arranged movable in parallel to its optical axis as driven by a driving mechanism 1020. The objective lens 403 is also driven by a driving mechanism 1030 for movement along the optical axis.

The multi pin hole 111 can be replaced with another multi pin hole 113 by section of a driving mechanism 1050. Similarly, the multi pin hole 141 can be replaced with another multi pin hole 143 by section of a driving mechanism 1060. The detector assembly 112 is arranged to select a mode for detecting the multi-beam light through not the multi pin holes 111 and 113. The detector assembly 142 is allowed to detect the multi-beam light which has at least been passed through the multi pin hole.

The beam splitter 202 can be replaced with a half mirror 1041 by section of a driving mechanism 1040 for directing an optical sum of the transmission light and the reflection light to the detector assembly 112.

It is easy to reduce the time required for the inspection by scanning the substrate with the multiple beams. In practice, the scanning with the multiple beams for the inspection is a troublesome task. This embodiment employs the cofocal optical system which produces a higher level of the resolution and permits the multiple beams to be scanned over the substrate or object for reading data of a pattern to be inspected at a higher sensitivity. The third embodiment is characterized by simultaneous inspection through the transmission light and the reflection light, which is well known and advantageous, carried out in the multi-beam scanning cofocal optical system.

According to the third embodiment, the multi-beam transmitted light inspection and the multi-beam reflected light inspection can be conducted separately and simultaneously while both the transmission and reflection of the multi-beam light can be detected simultaneously. In particular, since simultaneous detection of the transmission and reflection of the multi-beam light is possible, either an electrical combining method for electrically combining the transmission light and the reflection light after optically detecting the two separately or an optical combining method for optically combining and then detecting the transmission light and the reflection light can be selected for implementing optimum operation.

The electrical combining method permits a detection signal of the transmitted light and a detection signal of the reflected light to be obtained separately and simultaneously so that the characteristic of each signal is easily identified. Also, the detection signals of the transmitted light and the reflected light can be used as parameters of the defect analyzing functions to accomplish a variety of requirements including defect extraction, defect identification, defect type analysis, and defect component analysis. The optical combining method produces a composite signal indicative of optical characteristics such as interference from the transmitted signal and the reflected signal. The composite signal can also be used for carrying out such a group of defect extraction, defect identification, defect type analysis, and defect component analysis.

In this embodiment, the cofocal optical system is utilized to detect at least the reflected light. The transmission light and the reflection light both are focused on one point on the detector after passed through the scanners where the illumination beams to the substrate are traversed, thus establishing the cofocal optical system which is hardly realized in the conventional inspection apparatus. Since the cofocal optical system is used for detecting the reflected light, the sensitivity for detection in the reflection type optical system which provides lower contrast can significantly be increased. Also, optical selectioning which is one of the best characteristics of the cofocal optical system is feasible thus ensuring the 3-D shape analysis of a defect or a dust. This process allows the defect to be distinguished from the dust and will make easy an examination whether the amendment or the rinsing is necessary.

As the simultaneous detection of the transmitted light and the reflected light is compatible with the cofocal optical system, the optical resolution of a scanned image is increased and also the resolution in signal processing will be improved. Accordingly, the optical substrate inspection apparatus has a higher sensitivity for defect detection than the conventional apparatuses. Moreover, since the defect inspection is compatible with the multi-beam scanning optical system and its sensitivity for detection is high, it will be conducted at a shorter period of time than that of the conventional apparatuses.

In the embodiment, the transmission light is optically transmitted through the substrate, reflected by the reflective mirror, passed again through the substrate, and directed to the detector assembly. Since the transmission light passes two times one specific point on the substrate, its signal contains a two times intesified quality of optical data of the substrate. Accordingly, the resolution with the transmission type optical system will be higher than that of the cofocal optical system. Also, the optical system includes no such an abundancy that the transmitted light through the substrate bypasses the substrate before reaching the detector assembly. This contributes to the minimum number of the components and the ease of the optical axis adjustment throughout the system.

The optical substrate inspection apparatus of this embodiment thus has a higher resolution than that of a common cofocal optical system, a higher data extraction capability for identifying defect and dust, a simpler construction of the optical system, and a higher operatability for improving the throughput.

(Fourth Embodiment)

According to the present invention, a novel cofocal, multi-beam, defect inspection apparatus where a plurality of light beams are focused on a substrate and scanned at a high speed along a main scanning direction while a table is moved in another direction vertical to the main scanning direction for implementing subscanning to inspect a pattern on the substrate.

The apparatus includes, as a novel feature of the present invention, a laser cofocal optical system provided for increasing the resolution of a scanned image and a multi-beam scanning optical system provided for minimizing the time for inspection.

Figure 14:
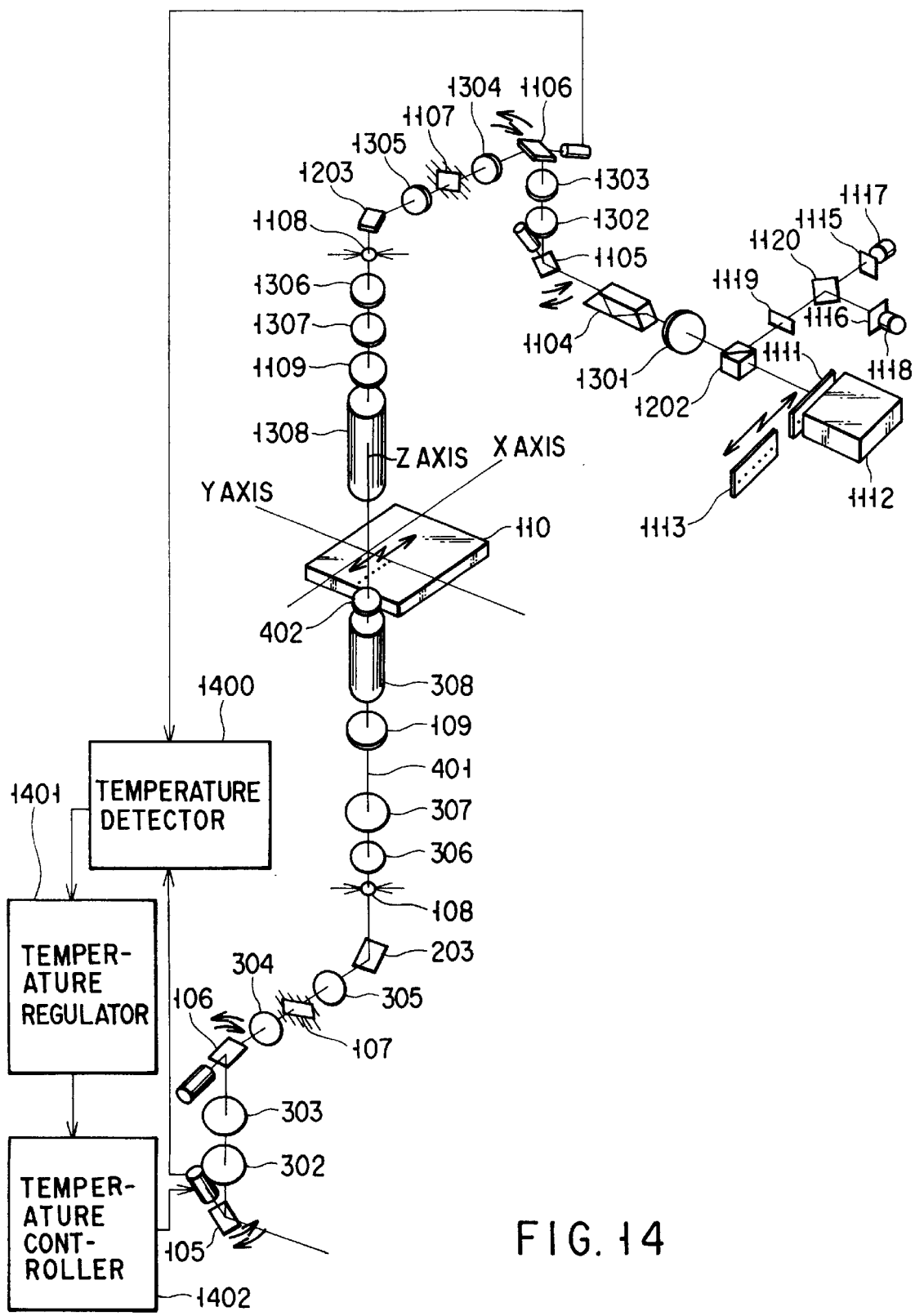
FIG. 14 is a view of a cofocal multi-beam scanning optical system in an optical substrate inspection apparatus according to a fourth embodiment of the present invention.

FIG. 14 illustrates a cofocal, multi-beam optical system in an optical substrate inspection apparatus according to the fourth embodiment of the present invention. The arrangement on the laser source side of a mirror 105 is identical to that shown in FIG. 2 and will be cited for ease of the description. Like components are denoted by like numerals as those shown in FIGS. 1 and 2 and will be explained in no more detail.

A linear polarized laser light emitted from a laser tube 100 is directed by a mirror 201 to a multi-beam generator 101. The multi-beam generator 101 may be of a filter type for generating a plurality of beams through their respective films. The multi-beam generator 101 causes one single beam of the light to split into multiple beams which are then directed to a multi lens 102. The multi lens 102 may be a group of small lenses, a micro lens of ion-exchange type, or a zone plate of a phase type. The multiple beams released from the multi-beam generator 101 and the multi lens 102 are converged.

The converged beams (a multi-beam light) are focused on pin holes in the multi pin hole 103. The multi pin hole 103 is essential in the cofocal optical system and has a plurality of pin holes therein of which diameter is determined by a degree of diffraction calculated from the optical constant of the multi lens 102. The multi-beam light from the multi pin hole 103 is directed to a polarized beam splitter 202. The multi-beam light has been linear polarized so that they can pass the polarized beam splitter 202 at optimum efficiency. The multi-beam light passing the polarized beam splitter 202 is further transmitted to a lens 301.

The multi-beam light is then directed via a rotating prism 104 to a scanner mirror 105. The rotating prism 104 is adjustable for determining The angle of the multi-beam light to a substrate of interest. The multi pin hole 103 and the scanner mirror 105 are arranged telecentric to each other by section of the lens 301. This allows the beams to be parallel to each other after the lens 301 and overlapped one another on the scanner mirror 105. The location of the scanner mirror 105 is conjugate to the location of an iris at an objective lens 308 so that its telecentric relationship on the substrate is established.

Two mirrors 105 and 106 are assembled to form a scanner for scanning along two axes, X-axis and Y-axis. The mirror 105 is provided for main scanning and the other 106 is for sub-scanning. Using the two axes, a limited area in a two-dimensional image can be read by scanning while the table remains stationary. The multi-beam light released from the two scanner mirrors 105 and 106 is then directed through two lenses 304 and 304 by which the conjugate location of the iris falls on a position denoted by 108. The numerical aperture NA on the substrate can thus be varied by controlling the flux of the multi-beam light at the iris location 108. Since the resolution will further be increased by setting an optimum shape of the iris, the aperture stop 108 can be replaced with another.

The multi-beam light passed through the aperture stop 108 is transmitted via lenses 306 and 307 and an objective lens 308 and focused on the substrate 110 to develop a row of beam spots spaced at equal intervals. Then, the multi-beam light is separated into a transmission light for transmitting through the substrate 110 and a reflection light for reflecting on the substrate 110. The transmitted light passing the substrate 110 is directed to a detector assembly 1112 via an optical path which is substantially equivalent to an optical path from the beam splitter 202 to the objective lens 308 where the laser light emitted from the laser source 100 runs. More particularly, the transmitted multi-beam light passing the substrate 110 is given to an objective lens 1308 which is telecentric to the substrate.

The multi-beam light passing through the objective lens 308 is directed via lenses 1307 and 1306, an aperture stop 1108, and lenses 1305 and 1304 to two scanners 1106 and 1105. Accordingly, the polarized condition developed by the X-axis scanner 105 is canceled by the X-axis scanner 1105 and returned to a stationary state. Also, the polarized condition developed by the Y-axis scanner 106 is canceled by the Y-axis scanner 1106 and returned to a stationary state. The multi-beam light released from the two scanners 1106 and 1105 is directed via a rotating prism 1104 and a lens 1301 to a multi pin hole 1111. The multiple section are converged by the multi pin hole 1111 and sent to the detector assembly 1112 where their signal intensities are measured separately.

The reflected multi-beam light reflected by the substrate 110 is passed again through the objective lens 308 and returned back to the two scanners 105 and 106 in an opposite direction. Accordingly, the Y-axis and X-axis polarized conditions of the multi-beam light are canceled by the Y-axis scanner mirror 106 and the X-axis scanner mirror 105 respectively and the multi-beam light is shifted back to its stationary state identical to the initial condition. The multi-beam light is further directed back to the rotating prism 104 which has been rotated back to its original state and returned to the polarized beam splitter 202.

The multi-beam light before directed to the substrate 110 is passed through a $\lambda/4$ plate 109 where its polarization is turned to a circular polarized condition. After reflected by the substrate 110, the multi-beam light is passed again through the $\lambda/4$ plate 109 where its polarization is turned 90 degrees to a linear polarized state. The reflected multi-beam light is then reflected on the polarized beam splitter 202 and directed to a multi pin hole 111. The multiple beams converged by the multi pin hole 111 are given to a detector assembly 112 where their signal intensities are measured separately.

The effect of polarization is used in the optical system for the purpose of increasing the light intensity efficiency and preventing any reflected component generated on a midway in the optical system from being received as a noise by the detector assembly. The multi pin holes 111 and 1111 have a row of pin holes of a small diameter therein which are essential for the cofocal optical system.

In the optical system of this embodiment, the multi-beam light is scanned along the X axis and the Y axis independently and its transmitted and reflected components are detected by their respective detectors as both have run through the cofocal optical system. The optical system of the embodiment is a multi-beam scanning, transmission type cofocal optical inspection system.

Similar to the third embodiment, the substrate 110 is loaded on a substrate holding mechanism for positioning in a Z-axis direction as well as the X-axis and Y-axis directions.

The multi pin holes 111 and 1111 can also be replaced by other multi pin holes 113 and 1113 respectively using driving mechanism not shown.

Although the optical system of the embodiment is designed for detection of both the transmitted light and the reflected light, its advantage may be equal to that of an optical system for detection of only the transmitted light. The following description will thus be made with the detection of the transmitted light.

As one feature in the embodiment, one pair of the scanners 105 and 106 for scanning the substrate 110 with the multiple beams is isolated from the other pair of the scanners 1105 and 1106 for directing the multi-beam light transmitted through the substrate 110 to the detector assembly 1112 in its stationary state. The two scanners 1105 and 1106 are synchronized with the corresponding scanners 105 and 106 for movement in the same cycle and in phase with or an integer multiple of 180 out of phase from each other.

While the angular movement is not identical in optical terms, the two scanners 1106 and 1105 are moved through the same angle as of the two scanners 106 and 105 respectively for ease of the description. This allows a polarized condition of the multi-beam light developed by the scanner 106 to be canceled by the corresponding scanner 1006 and a polarized condition of the multi-beam light developed by the scanner 105 to be canceled by the corresponding scanner 1005. As the result, the multi-beam light scanned on the substrate 110 in the X and Y directions can be received by the detector assembly 1112 in its stationary state.

Although the scanners of this embodiment are of a reciprocating oscillation type such as a galvanomirror, a resonance mirror, or an acousto-optic transducer, a rotary type such as a polygon mirror may be used with equal success. For converting the transmission type cofocal optical system to an ideal form, the multi-beam light transmitted through the substrate 110 may be bypassed from any optically desirable location in the optical path from the $\lambda/4$ plate 1109 to the scanner 1106 to any desirable location in the optical path from the $\lambda/4$ plate 109 to the scanner 106 and then, directed to the detector assembly 112 or a specific detector for detection of the transmitted light.

For the purpose, an optical bypass should be provided as an extension of the optical system to the scanners 105 and 106 via the substrate 110. The reason is that the multi-beam light is received by the detector assembly after its polarization is initialized by the corresponding scanner.

The optical system of this embodiment eliminates the need of such an optical path bypass. The optical system may have apparently a greater number of optical components than that of the conventional transmission type optical system provided with the bypass. The optical components can however be assembled in a more compact arrangement than the conventional one. While the structure of the bypass is determined by the size along the X and Y directions of the substrate 110, the stroke length for movement, and the dimensions of the substrate holding mechanism such as an XY stage on which the substrate 110 is loaded, the optical system of the embodiment is composed of two optical arrangements built on both sides of a base. The optical system rarely depends on the dimensions of the substrate or the substrate holding mechanism and its size will thus be avoided from enlargement.

Also, while the number of the optical components in the optical system of this embodiment is apparently greater than that of the conventional transmission type optical system provided with the bypass, the optical components provided along the path of the multi-beam light extending from the laser source to the detector assembly are minimized in the number.

As the bypass is extended from a node between the $\lambda/4$ plate 1109 and the scanner 1106 to a node between the $\lambda/4$ plate 109 and the scanner 106, the multi-beam light has to be returned back in symmetrical relationship about the substrate 110. The number of the optical components through which the multi-beam light passes from the laser source to the detector assembly is thus identical to that of the embodiment. For example, if the multi-beam light is bypassed before the $\lambda/4$ plate 1109, it has to return to after the $\lambda/4$ plate 109. If the multi-beam light is bypassed after the scanner 1106, it has to run back to before the scanner 106.

In addition, the use of the bypass requires a relay optical system including at least a relay lens and a mirror. The optical system of the embodiment however excludes such extra optical components and will hence decrease loss of the light intensity along the optical system. While the laser light passes the optical elements including lenses and mirrors, its intensity is declined. The optical system of the embodiment can eliminate such a loss without the relay optical system and its light intensity from the laser source will be utilized at a higher efficiency.

The amount of a given power from the laser source will be detected in a wider dynamic range as the multi-beam light after passing the substrate. For compensating the loss, the power of the laser source has to be increased. Since the optical system of the embodiment needs no such increase of the power of the laser source, its overall size will not be enlarged.

The scanner may be of a resonance type. The resonance type scanner typically comprises a mirror fixedly mounted to the distal end of a torsion bar. The natural frequency of the torsion bar is used for oscillating the mirror forward and backward along a twist direction of the torsion bar. The scanner made of the mirror is simple in the construction and easily reduced in the overall size. Also, as its moving part is light weighted and small in oscillation, the scanner of this type will often be used in a high-end optical apparatus.

However, the natural frequency is open controlled and may be varied wit time due to change in the temperature. The resonance scanners in this embodiment are scanned an integer multiple of 180° out of phase from each other and if their natural frequency is varied, may fail to focus each beam at one location on the corresponding detector.

For compensation, the optical system of the embodiment includes a temperature a controller for optimizing the temperature of the resonance scanners. More specifically, at least one of the paired resonance scanners is equipped with a temperature a controller which provides an optimum temperature condition over the two resonance scanners. For example, a current temperature of the two resonance scanners is detected with a temperature detector 1400 to determine a current rate of the natural frequency of the two scanners and a temperature controller 1402 in response to the current natural frequency changes the temperature or the natural frequency of the resonance scanners with a temperate regulator 1401. Accordingly, the scanning action will be stable in a long-run service while the temperature change is under control.

The defect inspection apparatus of the present invention is hence realized in that the sensitivity for detection of a transmitted light in the cofocal optical system is ideally increased and the overall construction is minimized in dimensions. The combination of the cofocal optical system and the multi-beam scanning optical system ensures the defect inspection at a higher sensitivity and within a shorter period of time. Also, the apparatus is minimized in the overall size, contributing to the decrease of the production cost.

(Fifth Embodiment)

Figure 15:
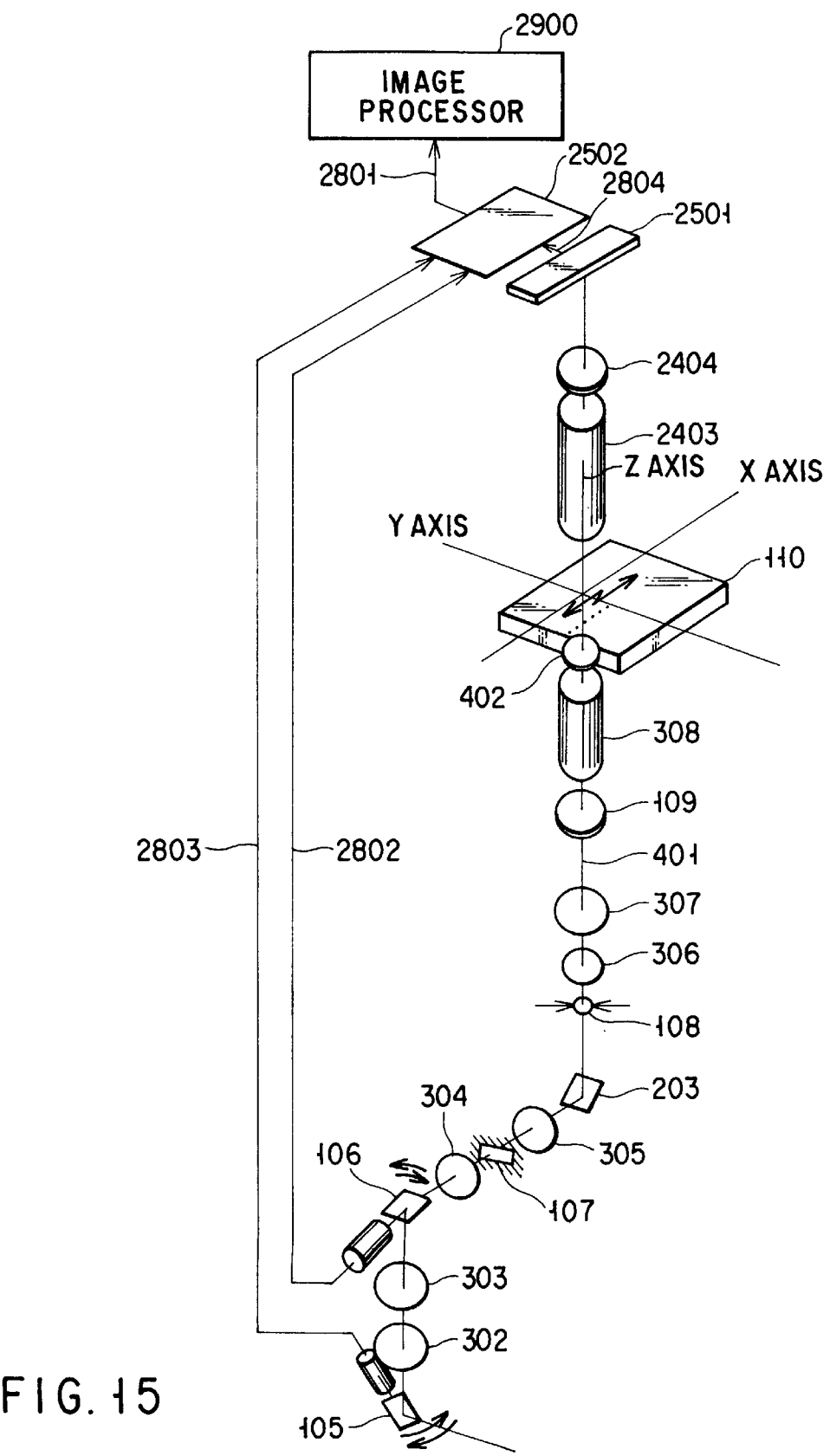
FIG. 15 is a view of a cofocal multi-beam scanning optical system in an optical substrate inspection apparatus according to a fifth embodiment of the present invention.

FIG. 15 illustrates a cofocal, multi-beam scanning optical system in an optical substrate inspection apparatus according to the fifth embodiment of the present invention. The arrangement on the laser source side of a mirror 105 is identical to that shown in FIG. 2 and will be cited. Like components are denoted by like numerals as those shown in FIGS. 1 and 2 and will be described in no more detail.

A linear polarized laser light emitted from a laser tube 100 is directed by a mirror 201 to a multi-beam generator 101. The multi-beam generator 101 may be of a filter type which divides the laser light into multiple beams through their respective films. The multi-beam generator 101 causes one single beam of the light to split into multiple beams which are then directed to a multi lens 102. The multi lens 102 may be a group of small lenses, a micro lens of ion-exchange type, or a zone plate of a phase type. The multiple beams released from the multi-beam generator 101 and the multi lens 102 are converged.

The converged beams (a multi-beam light) are focused on pin holes in the multi pin hole 103. The multi pin hole 103 is essential in the cofocal optical system and has a plurality of pin holes therein of which diameter is determined by a degree of diffraction calculated from the optical constant of the multi lens 102. The multi-beam light from the multi pin hole 103 is directed to a polarized beam splitter 202. The multi-beam light has been linear polarized so that they can pass the polarized beam splitter 202 at optimum efficiency. The multi-beam light passing the polarized beam splitter 202 is further transmitted to a lens 301.

The multi-beam light is then directed via a rotating prism 104 to a scanner mirror 105. The rotating prism 104 is adjustable for determining The angle of the multi-beam light to a substrate of interest. The multi pin hole 103 and the scanner mirror 105 are arranged telecentric to each other by section of the lens 301. This allows the beams to be parallel to each other after the lens 301 and overlapped one another on the scanner mirror 105. The location of the scanner mirror 105 is conjugate to the location of an iris at an objective lens 308 so that its telecentric relationship on the substrate is established.

Two mirrors 105 and 106 are assembled to form a scanner for scanning along two axes, X-axis and Y-axis. The mirror 105 is provided for main scanning and the other 106 is for sub-scanning. Using the two axes, a limited area in a two-dimensional image can be read by scanning while the table remains stationary. The multi-beam light released from the two scanner mirrors 105 and 106 is then directed through two lenses 303 and 304 by which the conjugate location of the iris falls on a position denoted by 108. The numerical aperture NA on the substrate can thus be varied by controlling the flux of the multi-beam light at the iris location 108. Since the resolution will further be increased by setting an optimum shape of the iris, the aperture stop 108 can be replaced with another.

The multi-beam light passed through the aperture stop 108 is transmitted via lenses 306 and 307 and an objective lens 308 and focused on the substrate 110 to develop a row of beam spots spaced at equal intervals. Then, the multi-beam light is separated into a transmission light for transmitting through the substrate 110 and a reflection light for reflecting on the substrate 110. The transmitted light passing the substrate 110 is directed to a detector assembly 2501 by an objective lens 2403 which is optically telecentric to the substrate.

The detector assembly 2501 comprises a succession of photosensitive elements, not shown, which produce and deliver detection signals 2804 to an element extractor 2502. The element extractor 2502 are responsive to scanning position signals 2803 and 2802 from the scanner 105 and 106 for determining the multi-beam scanning position on the substrate 110 and extracting from the detection signal 2804 a signal indicative of the multi-beam scanning position on the substrate 110. The extracted signal 2801 is then transferred to an image processor 2900.

The substrate 110 is loaded on a substrate holding mechanism not shown for movement in a Z axis direction as well as the X axis and Y axis directions.

Figure 16:
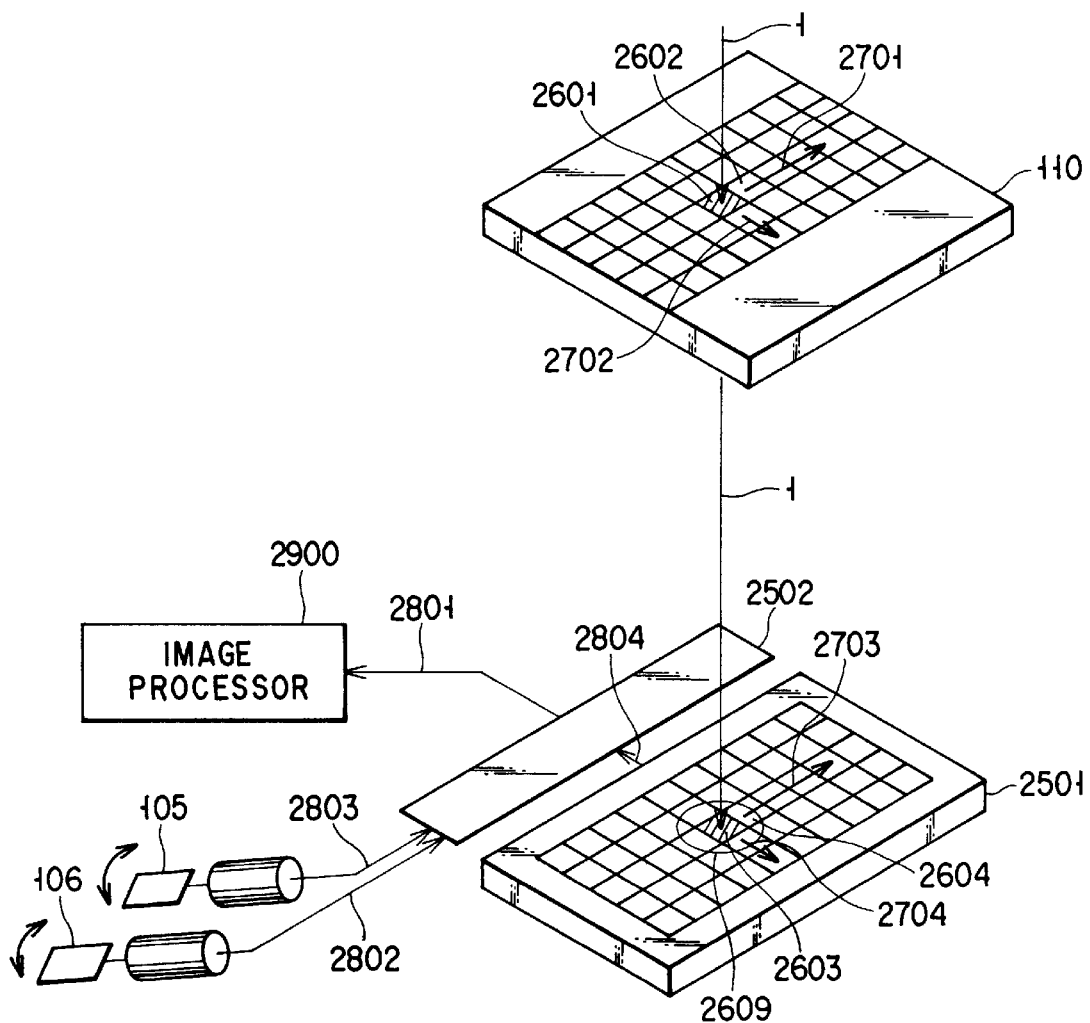
FIG. 16 is a view explaining a detecting action with the use of a single beam according to the embodiment shown in FIG. 15.

The detection of the beam scanned over the substrate 110 with the detector assembly 2501 is now explained. FIG. 16 shows the positional relation and the detection of the multi-beam light over the substrate 110 and the detector assembly 2501 in the optical system of the embodiment shown in FIG. 15. As shown in FIG. 16, one of the multiple beams is shown and denoted by 1 for ease of the description. Also, the multi-beam light in the embodiment is not limited to a plurality.

As the beam 1 has been passed across a pixel 2601 on the substrate 110 by the deflecting action of the scanner, it is focused on the photosensitive element 2603 of the detector assembly 2501. It is noted that the pixel 2601 is an exemplary unit area. Assuming that the data of a pattern produced through optically scanning the substrate 110 is subjected to arithmetical operations such as image processing, the substrate 110 is represented by a matrix of the pixels which are minimum units. The detector assembly 2501 also comprises the photosensitive elements which produce corresponding detection signals respectively. The pixel on the substrate 110 and the photosensitive element of the detector assembly 2501 are arranged in the cofocal optical system relationship.

The photosensitive element 2603 upon receiving the beam 1 produces a detection signal which is then transferred from the detector assembly 2501 to the element extractor 2502. The detection signals from their respective photosensitive elements of the detector assembly 2501 all are sent as the detection signal 2804 to the element extractor 2502. In common, the beam 1 entering the detector assembly 2501 is enlarged in cross section, as incident on the photosensitive element 2603, by the effect of various defect including aberration, flare, defocusing, and dispersion over the pattern on the substrate 110 which have been generated on the optical system before the beam 1 arrives at the detector assembly 2501. As shown in FIG. 16, the beam 1 is expanded, for example, to a circular area 2609. This causes the photosensitive elements about the center photosensitive element 2603 to produce detection signals.

In the cofocal optical system, one of the most important factors for producing a desired performance is the relation between the size of the pixel on the substrate 110 and the size of the photosensitive element of the detector assembly 2501. An ideal mode of the cofocal optical system increases the sensitivity for detection by limiting the incident of the light to a target area. Generally, a pin hole which is substantially identical in size to the photosensitive element 2603 is provided before the detector assembly.

In the fifth embodiment, the detection signal of the photosensitive element 2603 is selected and extracted by the element extractor 2502 out of the detection signal 2804 from the detector assembly 2501. The element extractor 2502 determines the current scanning position of the beam 1 on the substrate 110 from the scanning signals 2803 and 2802 of the scanners 105 and 106 and assigns the photosensitive element 2603 which corresponds to the scanning position. The detection signal of the photosensitive element 2603 corresponding to the scanning position is transferred as the detection signal 2801 to the image processor 2900. Accordingly, other components of the beam detected off the photosensitive element 2603 can be discarded as the effect of a pinhole.

With the cofocal optical system, it is most effective for high-speed scanning to scan the substrate with the beams. The beam 1 in the embodiment is controlled by the scanners for scanning over the substrate 110 along the main scanning direction 2701 and the subscanning direction 2702. This causes the beam 1 to be biased on the detector assembly 2501 in the main scanning direction 2701 and the subscanning direction 2702. For example, if the beam 1 is biased from a pixel 2601 to a pixel 2602, it is focused on a photosensitive element 2604 of the detector assembly 2501 which is assigned to the pixel 2602. At the time, the element extractor 2502 examines the scanning signals 2803 and 2802 from the scanners 105 and 106 to judge that the beam 1 is scanning on the pixel 2602 of the substrate 110 and selectively enables the photosensitive element 2604 assigned to the pixel 2602.

Thus, the detection signal of the photosensitive element 2604 is received as the detection signal 2801 by the image processor 2900. While the scanning signals from the scanners are used for determining the location of the pixel 2602 in the embodiment, any other section for detecting the scanning position on the substrate 110, such as a monitor for monitoring the angular movement of the scanners, may be used with equal success.

The resolution is now compared between a case (shown in FIGS. 17A to 17C) where the detection signals are delivered from their respective photosensitive elements regardless of the location of the scanning beam and a case (shown in FIGS. 17D to 17F) where the detection signal is delivered from only the photosensitive element which corresponds to the location of the scanning beam.

Figure 17A:
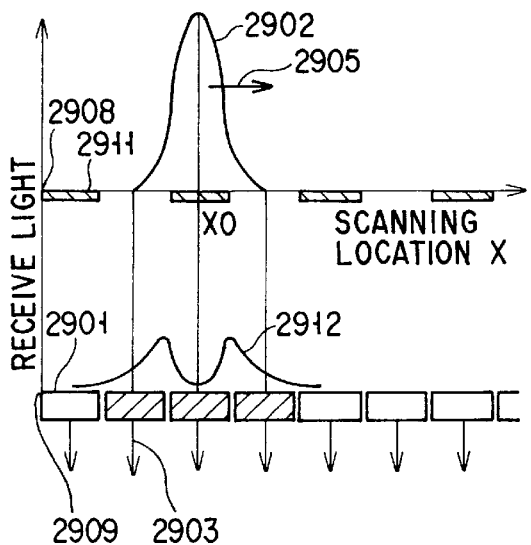
FIGS. 17A to 17F are diagrams showing comparison of the resolution between the detection signal of a not selected optical detector element and the detection signal of a specific optical detector element aligned with the location of the scanning beam.
Figure 17D:
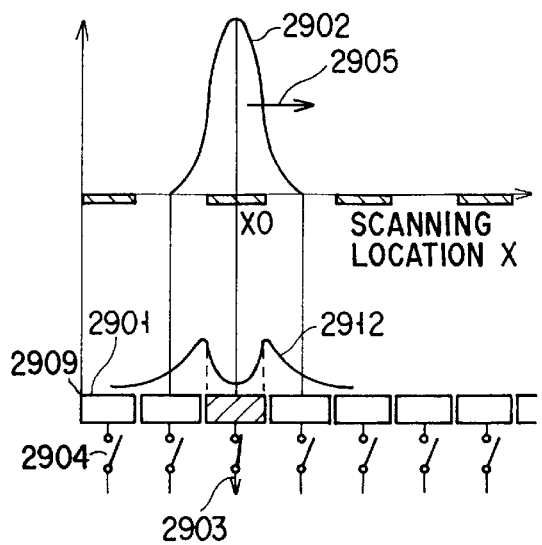

FIG. 17A schematically illustrates the incident light reading data at the scanning location x0 on a substrate 2908 and entering an optical detector 2909. A pattern of mask regions 2911 is developed on the substrate 2908. The optical detector 2909 comprises a group of photosensitive elements 2901. Each the photosensitive element 2901 produces a detection signal 2903. As the incident light of an intensity denoted by 2902 is scanned over the substrate 2908, its transmitted light through the substrate 2908 is received by the optical detector 2909 in an extended pattern 2912 modified by aberration and flare. Accordingly, extended portions of the transmitted light may be received by the neighbor photosensitive elements 2901 of the optical detector 2909 which do not correspond to the scanning location x0 but produce detection signals.

Figure 17B:
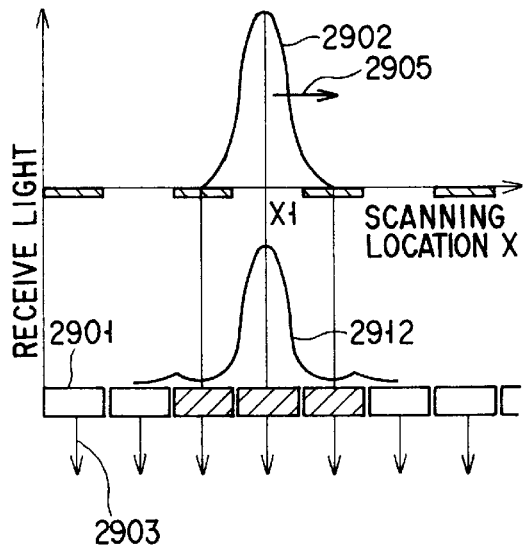

As the incident light is shifted in the scanning direction 2905, it scans the next scanning location x1 as shown in FIG. 17B. By repeating the shift in the scanning direction 2905, the received light triggers the photosensitive elements to producing detection signals which are then summed to have a signal of image data 2913 shown in FIG. 17C. The sum signal 2913 however contains crosstalk components picked up from the neighbor area of the target location of the element 2901 and hence will not represent data of the pattern on the substrate.

In the embodiment, contrast between the signal and thertifact is emphasized by the cofocal effect. FIG. 17D schematically shows the incident light reading data at the scanning location x0 on the substrate 2908 and entering the optical detector 2909. The optical detector 2909 comprises a group of the photosensitive elements 2901. Each the photosensitive element 2901 produces a detection signal 2903.

Similar to FIG. 17A, as the transmitted light through the substrate is received by the optical detector 2909, its extended portions may be received by the neighbor photosensitive elements 2901 of the optical detector 2909 which do not correspond to the scanning location x0. Advantageously, the detection signal from the photosensitive element corresponding to the scanning location x0 is only enabled in the embodiment. More specifically, selector switches 2904 assigned exemplarily to the respective scanning locations are turned on and off to enable the detection signal. Since the extended portions of the received light off the scanning location are electrically rejected, their artifacts including aberration and flare are eliminated.

Figure 17E:
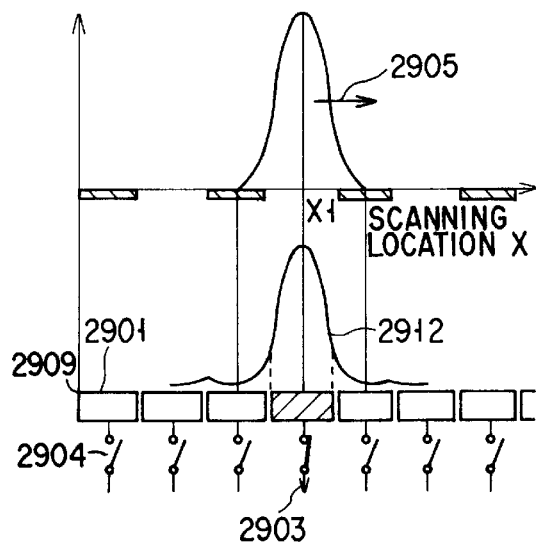
Figure 17C:
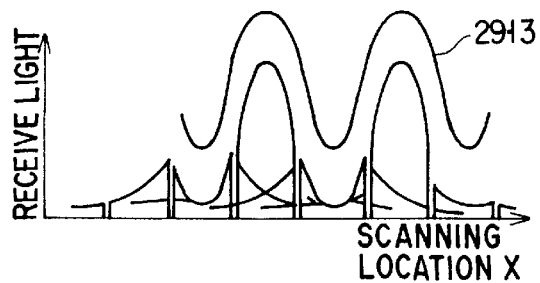
Figure 17F:
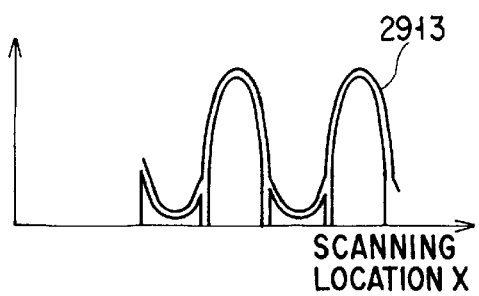

As the incident light is shifted in the scanning direction 2905, it scans the next scanning location x1 as shown in FIG. 17E. By repeating the shift in the scanning direction 2905, the received light triggers the photosensitive elements to producing detection signals which are then summed to have a signal of image data 2913 shown in FIG. 17F. As apparent, the sum signal 2913 based on the detection signals at the corresponding photosensitive elements 2901 includes non or less crosstalk components and its information will be accurate of the substrate pattern.

Figure 18:
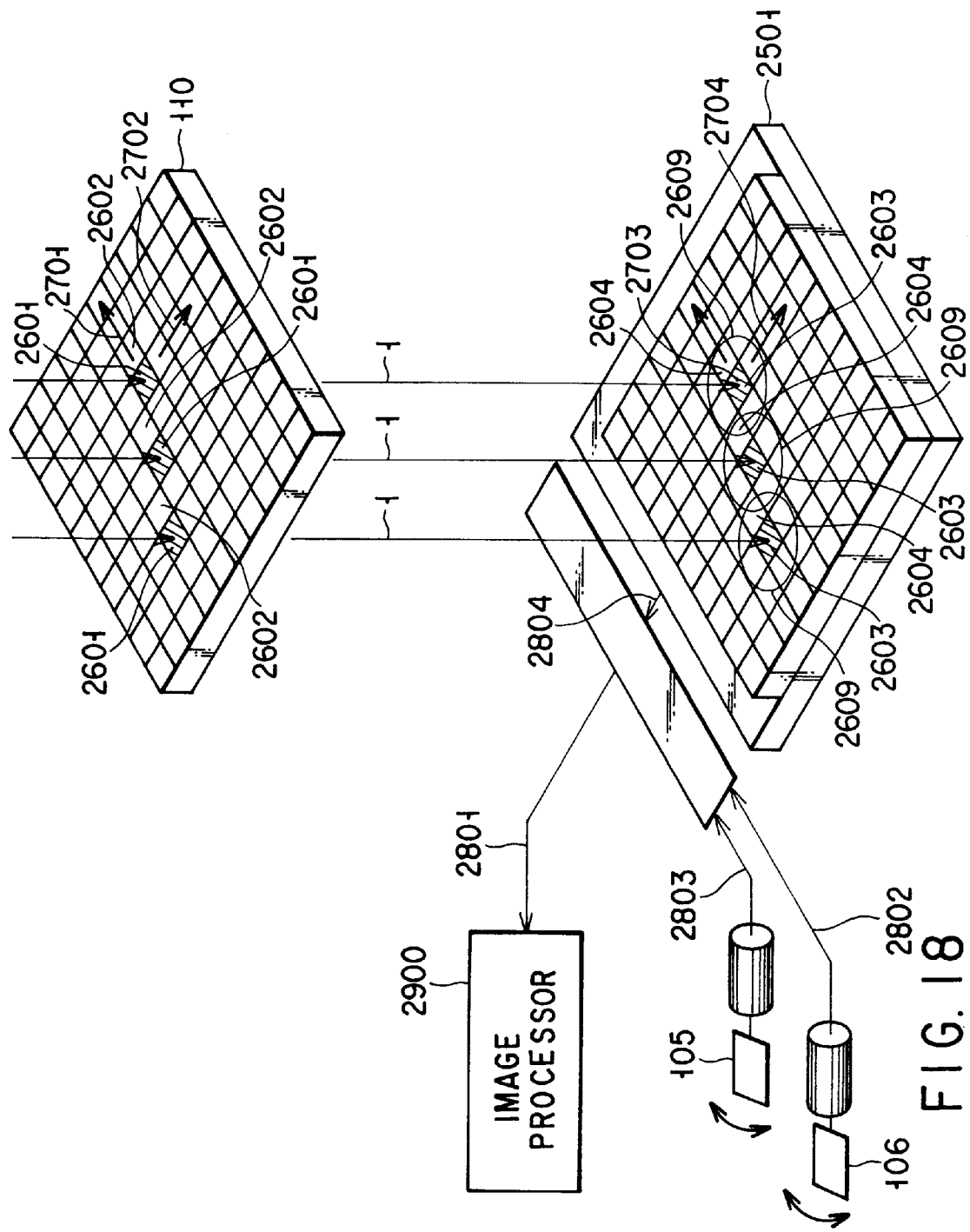
FIG. 18 is a view explaining a detecting action with the use of multiple beams according to the embodiment shown in FIG. 15.

The detecting action of the embodiment with the use of multiple beams is explained. FIG. 18 shows the relation of incident beams with a substrate 110 and a detector 2501 similar to that shown in FIG. 16. The arrangement is substantially identical to that shown in FIG. 16 except a plurality of the incident beams and will be explained in no more detail. The interval between the incident beams 1 is optically determined so as to prevent simultaneous illumination of two or more beams on a single pixel 2601 of the substrate 110 and simultaneous receipt of two or more beams by a single photosensitive element 2603 of the detector 2501. This is a fundamental requirement in the multi-beam scanning type cofocal optical system of the embodiment.

The scanning of the multiple beams is substantially identical to that of the single beam. The multiple beams 1 can be shifted by the scanner for scanning over the substrate 110 in the main scanning direction 2701 and the subscanning direction 2702. The multiple beams 1 are thus received by the detector 2501 as shifted correspondingly.

It is now assumed that the multiple beams 1 are shifted together from the pixel 2601 to another pixel 2602. Each of the multiple beams 1 is received by a photosensitive element 2604 of the detector 2501 which corresponds to the pixel 2602. The shift of the multiple beams 1 is not limited to one direction and they may be shifted independently in different cycles, amplitudes, and directions with equal success. As described above, the interval between the multiple beams 1 should optically be determined so as to prevent the simultaneous illumination of two or more beams on a single pixel 2601 of the substrate 110 and the simultaneous receipt of two or more beams by a single photosensitive element 2603 of the detector 2501.

Then, the scanning signals 2803 and 2802 of two scanners 105 and 106 are sent to an element extractor 2502 which in turn acknowledges that the pixel 2602 of the substrate 110 has been scanned by the multiple beams 1 and selectively enables the photosensitive element 2604 which corresponds to the pixel 2602. Accordingly, the detection signal of the photosensitive element 2604 only is transmitted as the detection signal 2801 to an image processor 2900.

Although the optical system for scanning the substrate 110 is of a transmission light type in this embodiment, a reflection light type may be used with equal success. The photosensitive element 2603 may be an assembly of tiny devices for improvement of the embodiment.

With the optical system of the fifth embodiment, multiple beams of light as well as a single beams of light can be scanned independently along the X axis and the Y axis and also, their scanned beams from the substrate can be utilized for the cofocal effect while being biased. As a result, an ideal mode of the cofocal optical system is realized for the inspection with both transmitted light and reflected light.

Now, it is not necessary to make the multiple beams stationary after scanning at a high speed over the substrate in the main scanning direction and the subscanning direction. Particularly when the detection with reflected light ion is used, the number of optical components from the light source to the detector is reduced to almost ½ hence minimizing the loss of the amount of the light. Accordingly, the increase of the size of the light source, the optical system, and thus the inspection apparatus is avoided. Subsequently, the price of the inspection apparatus is lowered and the efficiency of space utilization at a plant is improved. Therefore, the production cost will successfully be declined. In addition, the energy concentration about the light source is minimized and will thus be prevented from giving physical damage to the optical components and the substrate.

When the inspection with transmitted light is used, the bypass for the substrate is not needed. Accordingly, the overall arrangement of the optical system is decreased in the size and the number of the optical components from the light source to the detector is significantly reduced hence contributing to the more decrease of the overall size. It is understood that the substrate to be inspection is gradually increased in the dimensions within the years to come. In that respect, the present invention is advantageous. Also, the optical scanning section for canceling the polarization is eliminated and its related technical load such as antivibration precaution will be attenuated.

According to the embodiment, the transmission type cofocal optical system is implemented in an ideal mode for improvement of the inspection performance and the overall size of its inspection apparatus is minimized while providing a high-speed action of the multi-beam scanning.

As set forth above, the present invention permits multiple beams of laser light to scan the substrate to be inspection and their reflected or transmitted beams on the substrate to be detected separately to produce a scanned image of a higher resolution without increasing the inspection time. The present invention is thus advantageous as applicable to the defect inspection for a circuitry pattern of a future semiconductor device (such as a one-gigabit DRAM).

Since the aperture regulating members in the form of multi pin holes are employed for establishing the super resolution optical inspection system based on a favorable cofocal optical system, the resolution of a scanned image from the pattern will be improved significantly. In particular, the amount of a detection signal indicative of a minimal defect can be emphasized as compared with that of the conventional apparatus. The reflected light and the transmitted light are detected independently or simultaneously and the pattern on the substrate can thus be read in multiple aspects. Also, the resolution of the scanned image will be increased permitting the judgment whether the detection signal represents a detect or a dust.

According to the present invention, the sensitivity for detection of transmitted light can be improved in an ideal mode of the cofocal optical system while the overall dimensions of the defect inspection apparatus are minimized. The cofocal optical system and the multi-beam scanning optical system are operated in a better combination in the defect inspection apparatus of the present invention hence offering a higher level of the sensitivity for detection and significantly decreasing the inspection time. As its overall dimensions are minimized, the inspection apparatus will be used as a production machine lowering the production cost.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical substrate inspection apparatus for illuminating a substrate to be inspected with light and inspecting at least one of impurity and defect of a pattern formed on the substrate and foreign material on the substrate, comprising:

a laser source for generating a laser light to illuminate the substrate;

a beam splitter for splitting the laser light of the laser source into a plurality of beams;

a multi-beam scanner for scanning the substrate with the multiple beams;

an optical section for focusing the multiple beams independently on the substrate and directing at least one of reflected light and transmitted light of the multiple beams reflected on and transmitted th rough the substrate;

an optical detection section for detecting a change in the amount of each beam directed by the optical section;

groups of aperture regulating members disposed between the optical detection section at equal intervals corresponding to the intervals of the multiple beams directed from the substrate by the optical section for controlling the multiple beams;

a moveable table for continuously moving on a plane substantially vertical to the multiple beams and in a direction substantially perpendicular to the scanning direction of the multiple beams, comprising,
  an XY moving mechanism for independently moving along a reference plane or an XY plane substantially vertical to the optical path of the multiple beam, and
  a focusing moving mechanism which moves along a Z axis, which is the optical axis to compensate for changes in the focal points of the multiple beams;

an image generator for generating a two-dimensional scanned image in accordance with a detection signal from the optical detection section and a coordinate location of the moveable table; and a comparator for effecting a comparison between the two-dimensional scanned image from the image generator and a two-dimensional reference image.

2. An apparatus according to claim 1, further comprising:

groups of aperture regulating members disposed at equal intervals corresponding to the intervals of the multiple beams directed from the substrate for controlling the multiple beams; and an image rotator for changing The angle between the scanning direction determined by the multi-beam scanner and the direction of alignment of the multiple beams.

3. An apparatus according to claim 2, wherein the groups of aperture regulating members incorporate a group selected by an inspection mode from the groups of aperture regulating members which are prepared in advance and are different in aperture regulating member size and the image rotator is adjusted so as to have an optimum relation with the aperture regulating member size of the selected group of the groups of aperture regulating members.

4. An apparatus according to claim 2, wherein the groups of aperture regulating members incorporate a group selected by an inspection mode from the groups of aperture regulating members which are prepared in advance and are different in aperture regulating member size, and the image rotator is adjusted so as to have a predetermined relation with the aperture regulating member size of the selected group of the groups of aperture regulating members.

5. An apparatus according to claim 1, wherein the optical section comprises a section configured to direct the multiple beams from the substrate to pass through an optical path including the multi-beam scanner of the optical section, and to maintain the multiple beams stationary on the aperture regulating members while the multiple beams are scanned over the substrate.

6. An apparatus according to claim 1, wherein the optical section includes:
 a producing section for producing a linear polarized beam from the laser light of the laser source;
 optical polarization plate for polarizing the linear polarized beam for illuminating as a circular polarized beam on the substrate; and
 polarized beam splitter for splitting the reflected light from the substrate.

7. An apparatus according to claim 1, further comprising:
 a second multi-beam scanner for scanning the multiple beams in a Y-axis direction which is a second direction which is vertical to the main scanning direction which is a X-axis direction of the multi-beam scanner; and
 a controller for controlling a second multi-beam scanner in response to a signal indicative of the position of the movable table to produce a two-dimensional image of the XY plane on the substrate together with the multi-beam scanner.

8. An apparatus according to claim 1, further comprising:
 a second multi-beam scanner for scanning the multiple beams in a Y-axis direction which is a second direction which is vertical to the main scanning direction which is a X-axis direction of the multibeam scanner; and
 a controller for controlling the second a multibeam scanner in response to a signal indicative of the position of the movable table so that the multi-beam scanner scans to a target point along the Y axis direction as the movable table travels.

9. An apparatus according to claim 1, wherein the multi-beam scanner includes a scanner unit for scanning the multiple beams forward and backward along a direction substantially vertical to the moving direction of the movable table and for selecting one of the scanning signals produced by the forward and backward scanning which is desirable for the moving direction of the moveable table.

10. An apparatus according to claim 9, further comprising a passing and blocking unit provided at a desired location on the optical path extending from the laser source at least to the optical detection section for passing and blocking the multiple beams at intervals of a period and for a given duration.

11. An apparatus according to claim 1, wherein the optical section comprises:
 a first optical system for focusing the multiple beams on the substrate independently;
 a second optical system for directing the multiple beams of the transmitted light which have passed through the substrate;
 a substrate thickness measuring mechanism for measuring the thickness of the substrate; and
 a substrate thickness compensating mechanism responsive to a measurement from the measuring mechanism for geometrically compensating for an aberration change derived from the thickness of the substrate.

12. An apparatus according to claim 1, wherein the optical detection section comprises a first optical detector for detecting a change in the amount of the reflected light reflected by the substrate and a second optical detector for detecting a change in the amount of the transmitted light transmitted through the substrate, the first optical detector arranged at least for detecting a change in the amount of the multiple beams of the groups of aperture regulating members.

13. An apparatus according to claim 1, further comprising:
 a mirror provided across the optical path in the rear of the substrate for reflecting only the transmitted light so that the transmitted light from the substrate is reflected by the mirror, passed again through the substrate; and
 a second optical detector for receiving the light passed again through the substrate.

14. An apparatus according to claim 1, wherein the transmitted light and the reflected light of the multiple beams are substantially aligned with each other at the scanning position on the substrate.

15. An optical substrate inspection apparatus for illuminating a substrate to be inspected with light and inspecting, at least one of impurity and defect of a pattern formed on the substrate and foreign material on the substrate, comprising:
 a laser source for generating a laser light to illuminate the substrate;
 a beam splitter for splitting the laser light of the laser source into a plurality of beams;
 a multi-beam scanner for scanning the substrate with the multiple beams;
 an optical section for focusing the multiple beams independently on the substrate and directing at least one of reflected light and transmitted light of the multiple beams reflected on and transmitted through the substrate; and
 an optical detection section for detecting a change in the amount of each beam directed by the optical section, comprising,
 a plurality of detectors for detecting a change in the amount of the reflected light and performing at least one of offset-gain control and compensation for the change in the amount of light other than the amount of reflected light reflected from the substrate.

16. An apparatus according to claim 15, wherein the optical detection section includes detectors for detecting a change in the amount of some of the multiple beams from the laser source and transmit the change in the amount to a light amount correcting function of each detector to enable the compensation for the change in the amount at real time.

17. An optical substrate inspection apparatus for illuminating a substrate to be inspected with light and inspecting at least one of impurity and defect of a pattern formed on the substrate and foreign material on the substrate, comprising:
 a laser source for generating a laser light to illuminate the substrate;
 a beam splitter for splitting the laser light of the laser source into a plurality of beams;

a multi-beam scanner for scanning the substrate with the multiple beams;

an optical section for focusing the multiple beams independently on the substrate and directing at least one of reflected light and transmitted light of the multiple beams reflected on and transmitted through the substrate;

an optical detection section for detecting a change in the amount of each beam directed by the optical section;

groups of aperture regulating members disposed between the optical detection section at equal intervals corresponding to the intervals of the multiple beams directed from the substrate by the optical section for controlling the multiple beams;

a moveable table for continuously moving on a plane substantially vertical to the multiple beams and in a direction substantially perpendicular to the scanning direction of the multiple beams;

an image generator for generating a two-dimensional scanned image in accordance with a detection signal from the optical detection section and a coordinate location of the moveable table; and a comparator for effecting a comparison between the two-dimensional scanned image from the image generator and a two-dimensional reference image, wherein the moving speed v of the movable table is obtained from:

$$v = NAf$$

where the number of the multiple beams is n, the diameter of a beam spot on the substrate is a (=a'/b) which is determined by the pinhole diameter a' of the aperture regulating members and the optical magnification be and the scanning frequency of the multi-beam scanner is f.

18. An optical substrate inspection apparatus for illuminating a substrate to be inspected with light and inspecting at least one of impurity and defect of a pattern formed on the substrate and foreign material on the substrate, comprising:

a laser source for generating a laser light to illuminate the substrate;

a beam splitter for splitting the laser light of the laser source into a plurality of beams;

a multi-beam scanner for scanning the substrate with the multiple beams;

an optical section for focusing the multiple beams independently on the substrate and directing at least one of reflected light and transmitted light of the multiple beams reflected on and transmitted through the substrate;

an optical detection section for detecting a change in the amount of each beam directed by the optical section;

groups of aperture regulating members disposed at equal intervals corresponding to the intervals of the multiple beams directed from the substrate for controlling the multiple beams;

a first optical deflecting element for deflecting the multiple beams before directing them from the substrate to the groups of aperture regulating members;

a second optical deflecting element for deflecting the multiple beams once again;

groups of auxiliary aperture regulating members which are different in the diameter from each other and from the groups of aperture regulating members and control a part or all of the multiple beams of two lines produced by the second deflecting element; two auxiliary detectors for detecting the amount of the multiple beams controlled by the groups of auxiliary aperture regulating members; and a control circuit for processing signal outputs of the auxiliary detectors to generate an automatic focusing signal.

19. An apparatus according to claim 18, wherein a blocking unit for blocking the multiple beams is located at a desired location on the optical path extending from the laser source at least to the substrate.

20. An optical substrate inspection apparatus for illuminating a substrate to be inspected with light and inspecting at least one of impurity and defect of a pattern formed on the substrate and foreign material on the substrate, comprising:

a laser source for generating a laser light to illuminate the substrate;

a beam splitter for splitting the laser light of the laser source into a plurality of beams;

a multi-beam scanner for scanning the substrate with the multiple beams;

an optical section for focusing the multiple beams independently on the substrate and directing at least one of reflected light and transmitted light of the multiple beams reflected on and transmitted through the substrate comprising, a first optical system for focusing the multiple beams on the substrate independently, a second optical system for directing the multiple beams of the transmitted light which have passed through the substrate, a substrate thickness measuring mechanism for measuring the thickness of the substrate, and a substrate thickness compensating mechanism responsive to a measurement from the measuring mechanism for geometrically compensating for an aberration change derived from the thickness of the substrate; and an optical detection section for detecting a change in the amount of each beam directed by the optical section, wherein the substrate thickness compensating mechanism is a transmission optical device provided across the optical path for changing its thickness along the optical path.

21. An optical substrate inspection apparatus for illuminating a substrate to be inspected with light and inspecting at least one of impurity and defect of a pattern formed on the substrate and foreign material on the substrate, comprising:

a laser source for generating a laser light to illuminate the substrate;

a beam splitter for splitting the laser light of the laser source into a plurality of beams;

a multi-beam scanner for scanning the substrate with the multiple beams;

an optical section for focusing the multiple beams independently on the substrate and directing at least one of reflected light and transmitted light of the multiple beams reflected on and transmitted through the substrate, comprising, a first optical system for focusing the multiple beams on the substrate independently, a second optical system for directing the multiple beams of the transmitted light which have passed through the substrate, a substrate thickness measuring mechanism for measuring the thickness of the substrate, and a substrate thickness compensating mechanism responsive to a measurement from the measuring mechanism for geometrically compensating for an aberration change derived from the thickness of the substrate; and an optical detection section for detecting a change in the amount of each beam directed by the optical section, wherein the substrate thickness compensating mechanism is a lens assembly having at least one lens provided across the optical path for changing its location along the optical path to compensate for the aberration change.

* * * * *